US006932827B2

(12) United States Patent
Cole

(10) Patent No.: US 6,932,827 B2
(45) Date of Patent: Aug. 23, 2005

(54) METHODS AND DEVICES USING MAGNETIC FORCE TO FORM AN ANASTOMOSIS BETWEEN HOLLOW BODIES

(75) Inventor: David H. Cole, San Mateo, CA (US)

(73) Assignee: Medtronic, Inc., Minneapolis, MN (US)

(*) Notice: Subject to any disclaimer, the term of this patent is extended or adjusted under 35 U.S.C. 154(b) by 309 days.

(21) Appl. No.: 10/090,199

(22) Filed: Mar. 4, 2002

(65) Prior Publication Data

US 2002/0103495 A1 Aug. 1, 2002

Related U.S. Application Data

(63) Continuation of application No. 09/562,599, filed on Apr. 29, 2000, now Pat. No. 6,352,543.

(51) Int. Cl.[7] .............................................. A61B 17/11
(52) U.S. Cl. ...................... 606/153; 606/215; 128/898
(58) Field of Search ................................ 606/153, 215; 128/898

(56) References Cited

U.S. PATENT DOCUMENTS

| 3,986,493 A | 10/1976 | Hendren, III |
| 4,154,226 A | 5/1979 | Hennig et al. |
| 4,210,132 A | 7/1980 | Perlin |
| 4,258,705 A | 3/1981 | Sorensen et al. |
| 4,397,311 A | 8/1983 | Kanshin et al. |
| 4,679,546 A | 7/1987 | van Waalwijk van Doorn et al. |
| 4,809,713 A | 3/1989 | Grayzel |
| 4,889,120 A | 12/1989 | Gordon |
| 4,899,744 A | 2/1990 | Fujitsuka et al. |
| 4,904,256 A | 2/1990 | Yamaguchi |
| 5,330,486 A | 7/1994 | Wilk |
| 5,411,508 A | 5/1995 | Bessler et al. |
| 5,441,507 A | 8/1995 | Wilk |
| 5,507,629 A | 4/1996 | Jarvik |

(Continued)

FOREIGN PATENT DOCUMENTS

| DE | 29513195 | 12/1996 |
| DE | 29713335 | 7/1997 |

(Continued)

OTHER PUBLICATIONS

Esformes, et al., "Biological Effects of Magnetic Fields Generated with CoSm Magnets," pp. 81–87.

(Continued)

*Primary Examiner*—Julian W. Woo
(74) *Attorney, Agent, or Firm*—Tom Berry; Jeffrey J. Hohenshell

(57) ABSTRACT

Methods and devices for forming an anastomosis between hollow bodies utilizes magnetic force to couple anastomotic securing components and create a fluid-tight connection between the lumens of the hollow bodies. End-to-side, side-to-side and end-to-end anastomoses can be created without using suture or any other type of mechanical fasteners, although any such attachment means may be used in conjunction with the magnetic attachment. The securing components have magnetic, ferromagnetic or electromagnetic properties and may include one or more materials, for example, magnetic and nonmagnetic materials arranged in a laminated structure. The system of anastomotic securing components may be used in many different applications including the treatment of cardiovascular disease, peripheral vascular disease, forming AV shunts for dialysis patients, etc., and may be sized and configured for forming an anastomosis to a specific hollow body, for example, a coronary artery or the aorta.

26 Claims, 18 Drawing Sheets

U.S. PATENT DOCUMENTS

| | | | |
|---|---|---|---|
| 5,595,562 | A | 1/1997 | Grier |
| 5,611,689 | A | 3/1997 | Stemmann |
| 5,690,656 | A | 11/1997 | Cope et al. |
| 5,702,412 | A | 12/1997 | Popov et al. |
| 5,830,224 | A | 11/1998 | Cohn et al. |
| 5,895,404 | A | 4/1999 | Ruiz |
| 5,904,147 | A | 5/1999 | Conlan et al. |
| 5,906,579 | A | 5/1999 | Vander Salm et al. |
| 5,997,467 | A | 12/1999 | Connolly |
| 6,068,637 | A | 5/2000 | Popov et al. |
| 6,099,542 | A | 8/2000 | Cohn et al. |
| 6,173,715 | B1 | 1/2001 | Sinanan et al. |
| 6,190,353 | B1 | 2/2001 | Makower et al. |
| 6,352,543 | B1 * | 3/2002 | Cole .......................... 606/153 |

FOREIGN PATENT DOCUMENTS

| | | |
|---|---|---|
| RU | 2123300 | 12/1998 |
| SU | 736966 | 5/1980 |
| SU | 1025420 | 6/1983 |
| SU | 1179978 | 9/1985 |
| SU | 1438738 | 11/1988 |
| SU | RU 2018266 | 3/1989 |
| SU | 1537228 | 1/1990 |
| SU | 1595534 | 9/1990 |
| SU | 1629040 | 2/1991 |
| SU | 1635966 | 3/1991 |
| SU | 1277452 | 6/1991 |
| SU | 1708313 | 1/1992 |
| SU | 1361753 | 4/1992 |
| SU | 1725851 | 4/1992 |
| SU | 1766383 | 10/1992 |
| SU | 1769863 | 10/1992 |
| WO | WO 97/13463 | 4/1997 |
| WO | WO 97/27897 | 8/1997 |

OTHER PUBLICATIONS

Fuestel, et al., "Kontinente Kolostomie durch Magnetverschluβ," *Dtsch, Med. Wschr.* 100 (1975), pp. 1063–1064 (includes English Abstract).

Obora, et al., "Nonsuture Microvascular Anastomosis Using Magnet Rings: Preliminary Report," *Surg. Neurol.*, vol. 9, Feb. 1978, pp. 117–120.

Kanshin, et al., "Sutureless anastomoses in gastrointestinal surgery with and without steady magnetic field," *Arkh Patol,* 1978; 40(8):56–61 (with English Abstract).

Pirusyan, et al., "Some Regularities of Tissue Squeezing and Regeneration Under Formation of "Unstitch" Anastomoses of the Alimentary Canal's Hollow Organs,"1979, pp. 13–17 (includes English abstract).

Obora, et al., "Nonsuture Microvascular Anastomosis using Magnet Rings," Jan. 16, 1980, pp. 497–505. (English translation is provided.).

Yanase, "An Experimental Study on Traumatic Changes in Microvessels Produced by Pressure Clamping," *Aust N.Z. J. Surg*. vol. 50–No. 4, Aug., 1980, pp. 423–428.

Jansen, et al., "Clinical Applications of Magnetic Rings in Colorectal Anastomosis," *Surgery, Gynecology & Obstetrics*, vol. 153, Oct. 1981, pp. 537–545.

Myshkin, et al., "Use of Permanent Magnets in Sutureless Anastomoses," 1987, pp. 47–52. (English translation is provided.).

Kanshin, et al., "A Goal–Oriented Local Approach to the Prevention of Postoperative Purulent Complications," 1991, pp. 24–27. (English abstract is provided.).

Stepanov, et al., "The treatment of intestinal fistulae in children by applying a by–pass anastomosis using magnetic devices," *Khirugiia (Mosk)*, Nov.–Dec. 1992, pp. 11–12. (English abstract is provided.).

Fukumura, et al., "Development of a Magnetically Operated Artificial Urethral Sphincter," *ASAIO Journal*, 1993, pp. M283–M287.

Bondemark, et al., "Orthodontic Rare Earth Magnets —In Vitro Assessment of Cytotoxicity," *British Journal of Orthodontia*, vol. 21, No. 4, Nov. 1994, pp. 335–341.

Cope, "Evaluation of Compression oCholecystogastric and Cholecystojejunal Anastomoses in Swine after Peroral and Surgical Introduction of Magnets," *Journal of Vascular and Interventional Radiology*, vol. 6, No. 4, Jul.–Aug. 1995, pp. 546–552.

Cope, "Creation of Compression Gastroenterostomy by Means of the Oral, Percutaneous, or Surgical Introduciton of Magnets: Feasibility Study in Swine," *Journal of Vascular and Interventional Radiology*, vol. 6, No. 4, Jul.–Aug. 1995, pp. 539–545.

Bondemark, et al., "Long–term effects of orthodontic magnets on human buccal mucosa—a clinical, histological and immunohistochemical study," *Eur J Orthod*, 20(3): Jun. 1998, pp. 211–218.

Cope, "Stent Placement of Gastroenteric Anastomoses Formed by Magnetic Compression," *Journal of Visceral Intervention*, vol. 10, No. 10, Nov.–Dec. 1999, pp. 1379–1386.

\* cited by examiner

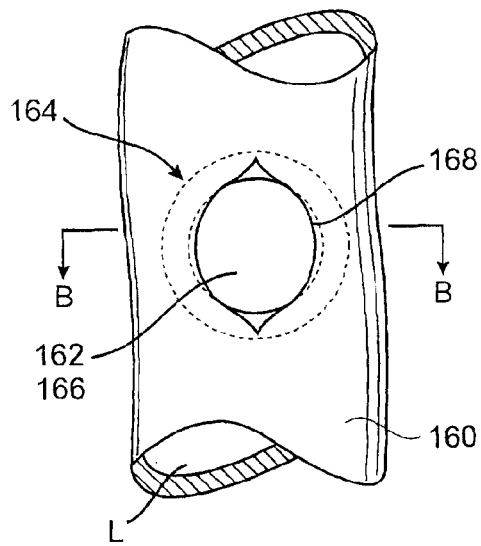
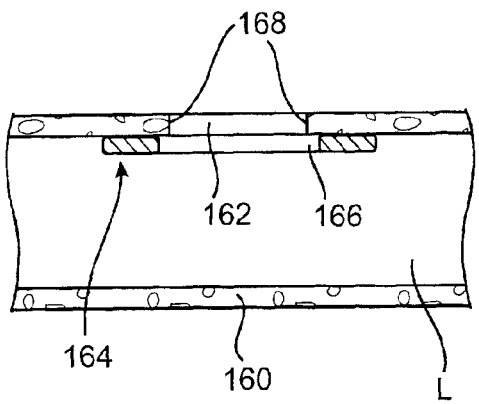
FIG. 17A     FIG. 17B
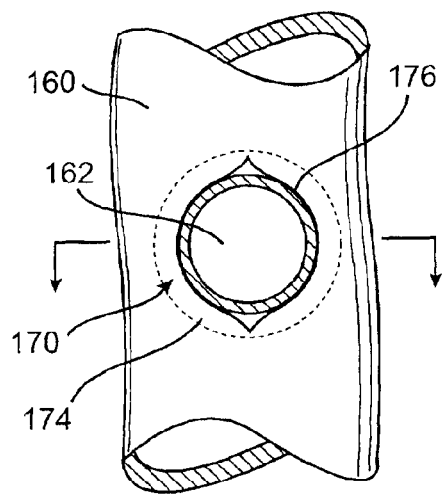
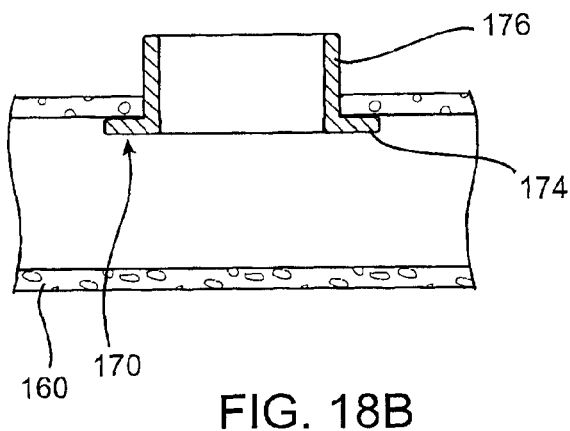
FIG. 18A     FIG. 18B

METHODS AND DEVICES USING MAGNETIC FORCE TO FORM AN ANASTOMOSIS BETWEEN HOLLOW BODIES

CROSS-REFERENCE TO RELATED APPLICATION

This application is a continuation of application Ser. No. 09/562,599, filed Apr. 29, 2000 U.S. Pat. No. 6,352,543. The complete disclosure of the aforementioned related U.S. patent application is hereby incorporated herein by reference for all purposes.

BACKGROUND OF THE INVENTION

1. Field of the Invention

The invention relates to methods and devices for forming an anastomosis between two hollow bodies, and more particularly to forming an anastomosis using magnetic force.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue to search for new treatments and improvements to existing treatments.

Coronary artery disease is currently treated by interventional procedures such as percutaneous transluminal coronary angioplasty (PTCA), coronary stenting and atherectomy, as well as surgical procedures including coronary artery bypass grafting (CABG). The goal of these procedures is to reestablish or improve blood flow through occluded (or partially occluded) coronary arteries, and is accomplished, for example, by enlarging the blood flow lumen of the artery or forming a bypass that allows blood to circumvent the occlusion. What procedure(s) is used typically depends on the severity and location of the blockage. When successful, these procedures restore blood flow to myocardial tissue that had not been sufficiently perfused due to the occlusion.

Another proposed treatment places the target vessel, e.g., a coronary artery, in direct fluid communication with a heart chamber containing blood, for example, the left ventricle. Blood flows from the ventricle into a conduit that is in fluid communication with the artery; as such, this treatment may be described as a ventricular bypass procedure. Benefits of this procedure include obviating the need to manipulate the aorta, for example, as is done when a side-biting clamp is used in a typical CABG procedure to create a proximal anastomosis between the bypass graft and the aorta. Clamping or otherwise manipulating the aorta places the patient at risk in some cases due to the likelihood that such manipulation will release embolic material into the bloodstream. Some challenges associated with this procedure include delivering and deploying the conduit in the patient's body, properly positioning the conduit with respect to the heart chamber and the target vessel, and obtaining beneficial flow characteristics through the conduit and the target vessel.

A particularly challenging task that must be performed during CABG procedures (as well as some ventricular bypass procedures) is suturing the conduit to one or more vessels. As an example, one end of the conduit may be sutured to a source of blood, such as the aorta, a heart chamber or a blood vessel, while the other end of the conduit is sutured to the target vessel, such as a coronary artery or another blood vessel. The small diameter of the vessels involved (typically from 1 mm to 4 mm) makes creating a handsewn anastomosis a highly technical and time-consuming procedure. The difficulty in forming the sutured anastomosis is exacerbated when access to the target vessel is restricted or limited, as in a minimally invasive or percutaneous procedure. This problem also arises in non-cardiovascular applications that utilize handsewn anastomoses, for example, treating peripheral vascular disease or injury, creating AV (arteriovenous) shunts, etc.

While those in the art have proposed various anastomotic couplings intended to replace a sutured anastomosis, none has performed well enough to receive any significant level of acceptance in the field. Many of the proposed couplings penetrate or damage the target vessel wall acutely or chronically, do not remain patent, fail to produce a fluid-tight seal between the conduit and vessel, or are simply too cumbersome and difficult to deliver or deploy.

Accordingly, there is a need in the art for methods and devices for forming a reliable anastomosis between hollow bodies in a relatively quick, easy and repeatable manner as compared to handsewn anastomoses or anastomoses formed by prior art, suture-free devices.

SUMMARY OF THE INVENTION

According to one embodiment, the invention provides a method using magnetism for forming an anastomosis between first and second hollow bodies. Each hollow body has a lumen and an opening extending into the lumen. The method is carried out by positioning a first securing component adjacent the opening in the first hollow body, positioning a second securing component adjacent the opening in the second hollow body, and using magnetic force to form an anastomosis between the first and second hollow bodies with the lumens of the first and second hollow bodies in communication.

According to another embodiment, the invention provides a method using magnetism for forming an anastomosis between first and second hollow bodies, each of which has a lumen. The method uses magnetic force to form an anastomosis between first and second hollow bodies so as to place their lumens in communication. The first hollow body has proximal and distal portions between which the anastomosis is disposed.

According to another embodiment, the invention provides a method using magnetism for forming an anastomosis between first and second hollow bodies with lumens and openings extending into the lumens. This method is performed by positioning a first securing component adjacent an opening in the first hollow body, positioning a second securing component adjacent an opening in the second hollow body, and using magnetic force to form an anastomosis between the first and second hollow bodies with the lumens of the first and second hollow structures in communication. At least one of the securing components is positioned without everting the hollow body.

According to still another embodiment, the invention provides a method using magnetism for forming an anastomosis between first and second hollow bodies by positioning a first securing component adjacent the first hollow body, positioning a second securing component adjacent the second hollow body, and using magnetic force to control the relative position of the first and second securing components and to form an anastomosis between the first and second hollow bodies. The blood-carrying lumens of the first and second hollow bodies are placed in communication, with at least one of the first and second securing components at least partially disposed within the blood-carrying lumen of one of the first and second hollow bodies.

According to another embodiment of the invention, a method for forming an anastomosis between first and second hollow bodies may or may not use magnetism to facilitate the anastomosis. This method includes steps of positioning a first securing component through an opening in the wall of the first hollow body and at least partially within the lumen of the first hollow body, positioning a second securing component adjacent the second hollow body, applying a coupling force to the first and second securing components without penetrating the wall of the first hollow body, and forming a seal between the first and second hollow bodies while placing the lumens of the first and second hollow bodies in communication. The coupling force is applied at substantially the same location at which the seal is formed.

According to yet another embodiment, the invention provides a system for forming an anastomosis between first and second hollow bodies in a patient's body. The system includes first and second securing components capable of producing a magnetic field that applies force to maintain the securing components in a desired relative position. The first securing component has an opening and is substantially plate-shaped and sized and configured to be at least partially received in a lumen of a hollow body in a patient's body, and the second component has an opening and is sized and configured to be positioned adjacent a second hollow body in the patient's body for forming an anastomosis between the first and second hollow bodies.

BRIEF DESCRIPTION OF THE DRAWING FIGURES

FIG. 17A is a plan view of one of the hollow bodies and securing components shown in FIG. 12;

FIG. 17B is a longitudinal sectional view of the hollow body and securing component shown in FIG. 17A;

FIG. 18A is a plan view of the hollow body of FIGS. 17A–17B and a securing component constructed according to an alternative embodiment of the invention;

FIG. 18B is a longitudinal sectional view of the hollow body and securing component shown in FIG. 18A;

DETAILED DESCRIPTION OF PREFERRED EMBODIMENTS

The present invention relates to methods and devices for forming an anastomosis between first and second (or additional) hollow bodies located in a patient's body, for example, a connection between a graft vessel and coronary or peripheral blood vessels, viscera, reproductive ducts, etc. The anastomosis places the hollow bodies, more specifically the lumens of the hollow bodies, in communication. In the case of blood-carrying bodies (or other hollow bodies that carry fluid) the anastomosis places the bodies in fluid communication. The hollow bodies being joined may comprise native or autologous vessels, vessels formed of synthetic material such as ePTFE, DACRON®, etc.

Figure 1:
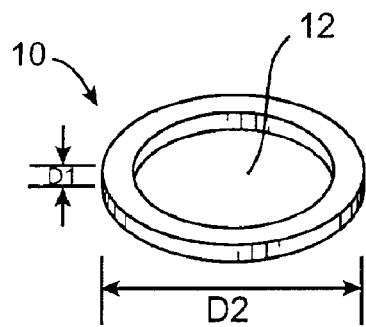
FIGS. 1–5 are perspective views of anastomotic securing components constructed according to various embodiments of the invention.

FIGS. 1–5 illustrate several exemplary embodiments of anastomotic securing components constructed according to the invention for use in forming an anastomosis between first and second hollow bodies. FIG. 1 shows a securing component 10 with an annular body and an opening 12 defined by the body. The component 10 is generally plate-shaped and circular in plan view with a constant (or substantially constant) thickness and width around its perimeter. The securing component 10 is sized and configured to be placed adjacent an opening of a first hollow body that has been prepared for anastomosis to a second hollow body. A second securing component would be placed adjacent an opening of the second hollow body for making the anastomotic connection.

Figure 2:
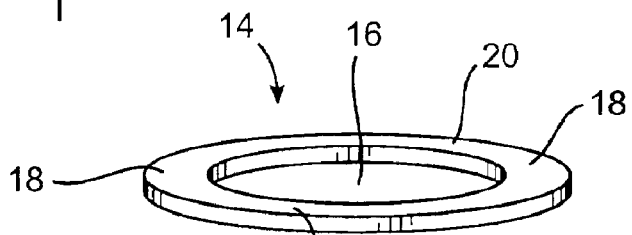
Figure 3:
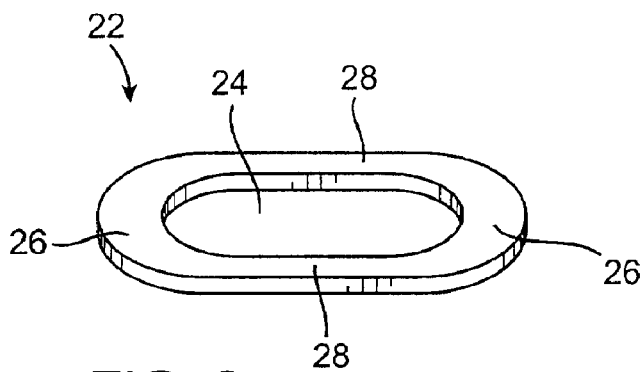
Figure 4:
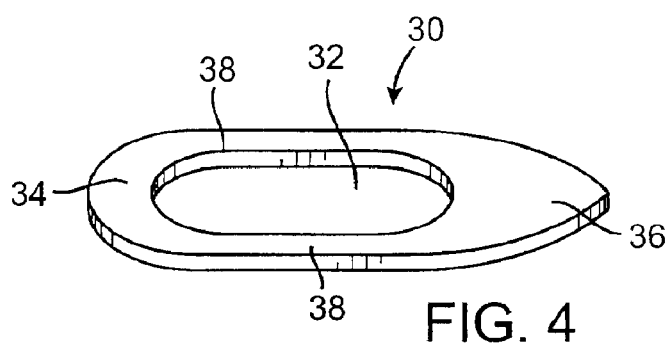

FIG. 2 shows an elliptical-shaped, anastomotic securing component 14 with an opening 16. The securing component 14 is generally plate-shaped and the opening 16 is configured to provide the securing component 14 with larger end portions 18 than side portions 20. FIG. 3 shows a racetrack-shaped securing component 22 with an opening 24. As in securing component 14, the opening 24 provides securing component 22 with larger end portions 26 than side portions 28. FIG. 4 shows a securing component 30 with an opening 32, two end portions 34, 36 and two side portions 38. The securing component 30 has a generally racetrack-shaped configuration, however, the end portion 36 is larger than the end portion 34 which provides the component 30 with an asymmetric configuration. Stated otherwise, the opening 32 is not centrally located with respect to the body of the component 30, unlike the openings 12, 16 and 24 of respective securing components 10, 14 and 22 shown in FIGS. 1–3. Also, the end 36 provides a tapered leading edge for easier introduction into a hollow body such as a blood vessel.

It will be understood that the specific shape and size of the securing components may be varied from the exemplary configurations depicted in FIGS. 1–4. For example, the thickness or width of the securing component may vary along all or part of the body of the component. The anastomotic securing components of the invention are preferably, though not necessarily, plate-shaped, i.e., a first dimension D1 of the component is less than a second dimension D2 of the component (FIG. 1). Typically, the lesser dimension corresponds to a thickness of the component while the larger dimension corresponds to a width or length of the component (or diameter in the case of FIG. 1). Minimizing the thickness of the securing component may be desirable for applications in which one or more components are placed within the lumen of a relatively small hollow body, e.g., a coronary artery, to reduce the amount of foreign material in the bloodstream and minimize flow impedance.

It will be noted that the securing components shown in FIGS. 1–4 are generally flat; however, they could instead be curved or arcuate, or comprise a combination of flat and curved sections. Additionally, in the illustrated and preferred construction the shape of each securing component substantially corresponds to the opening therein. That is, the securing component and its opening preferably have complementary configurations (e.g., elliptical component, elliptical opening). Nevertheless, the securing component could have a non-complimentarily-shaped opening. Finally, while each of the illustrated securing components includes only one opening, more than one opening could be used if desired.

According to preferred embodiments of the invention the anastomotic securing components are formed of or have incorporated therein a material capable of producing a magnetic field that acts to maintain the components in a desired positional relationship. The magnetic field results in the securing components maintaining the first and second hollow bodies in a desired position so as to be in fluid-tight communication. The material used to form one or both securing components is preferably magnetic, ferromagnetic or electromagnetic.

Figure 5:
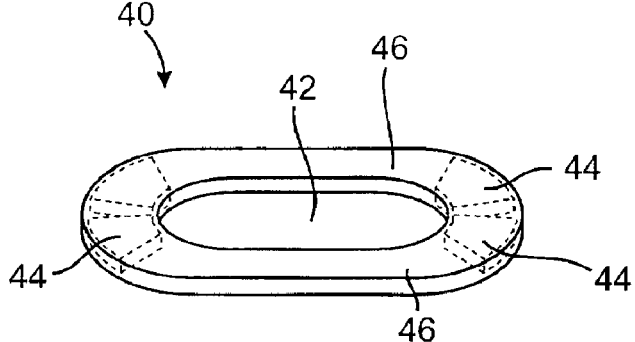

Each of the securing components shown in FIGS. 1–4 is formed substantially entirely of a suitable, magnetic field-producing material such that magnetic force may be generated over the entire area of the component. FIG. 5 shows an alternative embodiment wherein a securing component 40, which has an opening 42 and a racetrack-shaped configuration similar to securing component 22 of FIG. 3, has defined portions capable of producing a magnetic field. Specifically, the securing component 40 includes magnetic field-producing members 44 located at discrete areas which, in the illustrated embodiment, are at the ends of the component. The remaining areas 46 may thus be formed of a different material. It will be recognized that the members 44 could be located at alternative (or additional) areas of the securing component 40. An exemplary reason for providing the securing component 40 with areas 46 is to allow the use of a rigid magnetic material for the members 44 while still permitting the component to be partially or completely collapsed, for example, for delivery through a small incision or port, trocar, catheter, cannula, etc., by folding the areas 46.

Suitable materials that may be used to form an anastomotic securing component that is capable of producing a magnetic field include NdFeB (Neodymium Iron Boron), SmCo (Samarium Cobalt), and Alnico (Aluminum Nickel Cobalt). NdFeB is currently preferred for its force characteristics. The amount of force exerted will depend on various factors including the materials used, the size of the magnets and the number of magnets. In addition, different applications will call for different force ranges. For instance, it may be desirable to minimize the force as much as possible while still achieving a fluid-tight and secure attachment when treating small diameter blood vessels. As an example, in anastomosing coronary vessels, it is preferred to use anastomotic securing components that produce magnetic force in the area of less than 0.25 lbs, and more preferably approximately 0.15 lbs or less.

Figure 6:
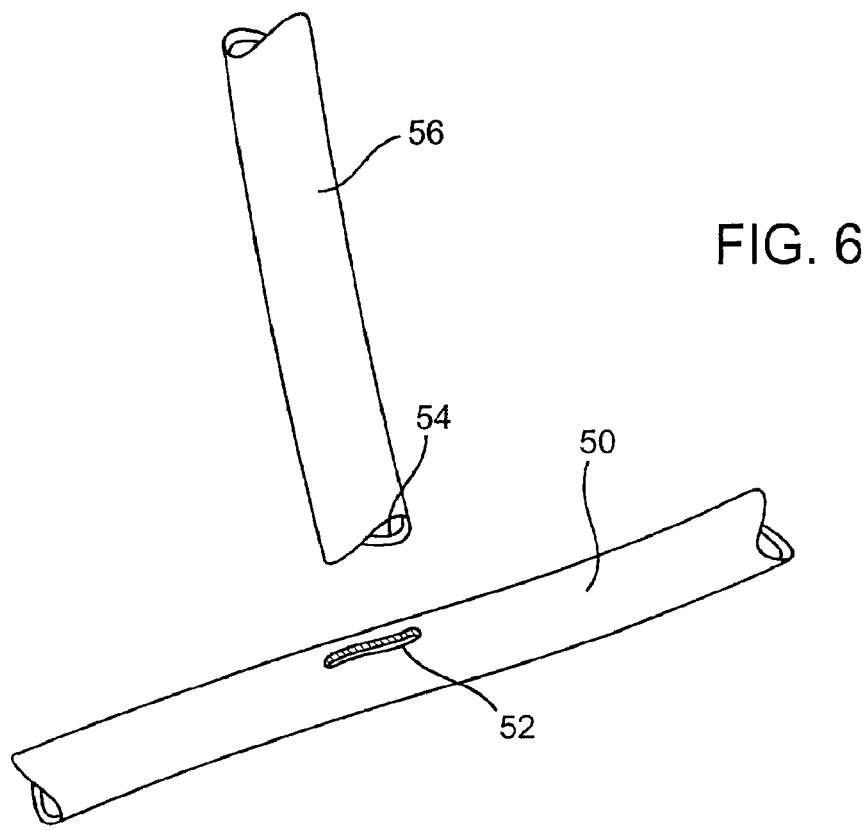
FIG. 6 is a perspective view showing two hollow bodies adapted to be joined in communication via an end-to-side anastomosis.
Figure 7:
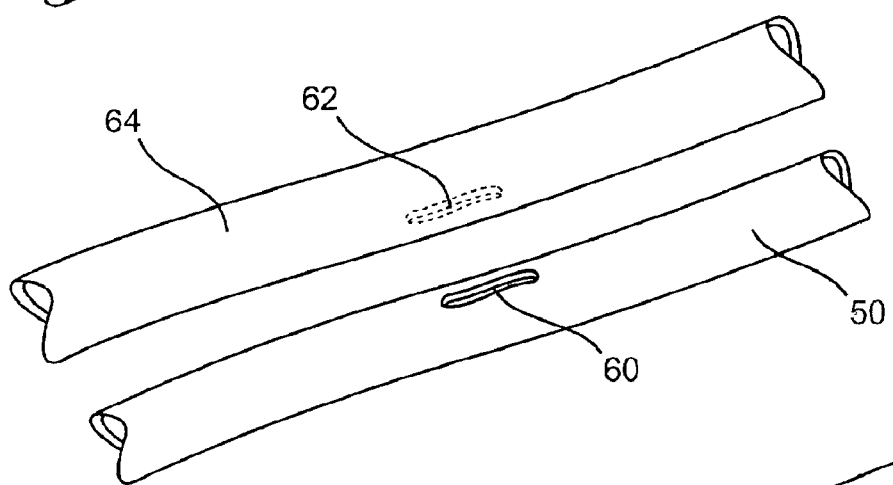
FIG. 7 is a perspective view showing two hollow bodies adapted to be joined in communication via a side-to-side anastomosis.
Figure 8:
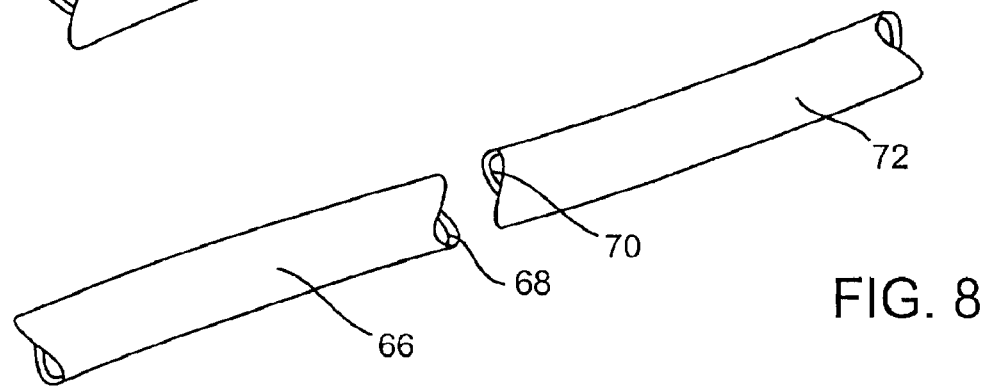
FIG. 8 is a perspective view showing two hollow bodies adapted to be joined in communication via an end-to-end anastomosis.

FIGS. 6–8 depict first and second hollow bodies that have been prepared for anastomosis in three different manners. FIG. 6 shows a first hollow body 50 with an opening 52 that is adapted to be joined to an opening 54 of a second hollow body 56 to form an end-to-side anastomosis. The completed anastomosis places the lumens of the respective hollow bodies in communication. The opening 52 is formed in the wall of the first hollow body 50, for example, by incising or punching the tissue of the wall, while the opening 54 is defined by an end of the second hollow body 56. FIG. 7 shows a first hollow body 58 with an opening 60 adapted to be joined to an opening 62 of a second hollow body 64, thereby forming a side-to-side anastomosis that places their lumens in communication. The openings 60, 62 are formed in the walls of the hollow bodies 58, 64, for example, as described above regarding opening 52. FIG. 8 shows a first hollow body 66 with an opening 68 adapted to be joined to an opening 70 of a second hollow body 72 to form an end-to-end anastomosis. Each opening 68, 70 is defined by an end of its associated hollow body 66, 72.

Figures 9, 9A:
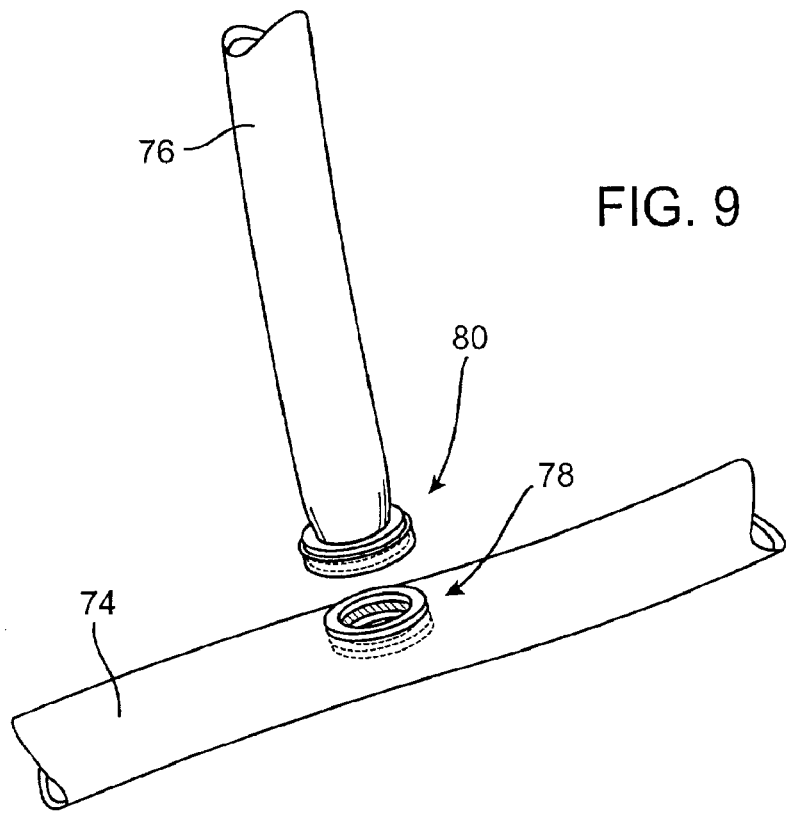
FIG. 9 is a perspective view of the two hollow bodies shown in FIG. 6 along with an anastomotic system including anastomotic securing components constructed according to one embodiment of the invention.
FIG. 9A is a sectional view of the anastomosis shown in FIG. 9.

FIGS. 9 and 9A show first and second hollow bodies 74, 76 respectively provided with first and second anastomotic securing components 78, 80 which are used to create an exemplary end-to-side anastomosis according to one embodiment of the invention. As shown best in FIG. 9A, the securing component 78 includes two members 78A, 78B disposed on opposite surfaces of a wall of the first hollow body 74. The securing component 80 includes two members 80A, 80B disposed on opposite surfaces of an everted end of the second hollow body 76. The members forming each securing component 76, 78 may be held in a desired and preferably fixed relative position by magnetic force, with magnetic force also being used to hold the two securing components in position. The securing components 78, 80 are moved together from the position of FIG. 9A to create a fluid-tight anastomosis.

Figure 10A:
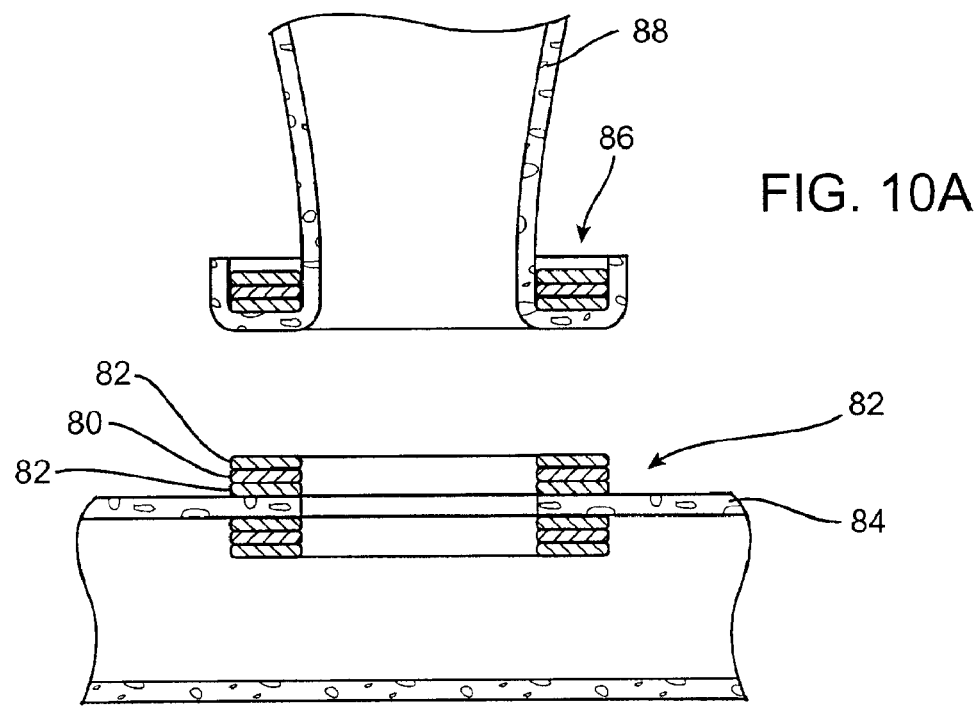
FIG. 10A is a section view similar to FIG. 9A but including alternative anastomotic securing components used to join the two hollow bodies.

FIGS. 10A–10D depict additional end-to-side anastomoses formed according to other embodiments of the invention. FIG. 10A shows a first securing component 82 coupled to a first hollow body 84 and a second securing component 86 coupled to a second hollow body 88. The securing components 82, 86 have a laminated structure comprising a layer of material 80 capable of producing a magnetic field disposed between two layers of material 82. The material 82 may also be capable of producing a magnetic field or, alternatively, ferromagnetic or non-ferromagnetic, and may comprise a metal, polymer, ceramic, etc.

One exemplary application of this particular feature of the invention comprises a securing component with a middle layer of NdFeB (Neodymium Iron Boron—magnetic) and two outer layers of 302 stainless steel (non-magnetic). The outer layers are bonded by suitable adhesive to the middle layer. Alternatively, the two outer layers could comprise a magnetic material, e.g., 440C stainless steel, surrounding a middle layer that is either magnetic or non-magnetic. As an example, the securing component may comprise a 0.008 inch thick magnetic layer and two 0.001 inch outer steel layers. It will be understood that this aspect of the invention may be practiced using other materials.

A benefit of this construction is that it allows the thickness of the magnetic layer to be reduced (which makes the brittle magnet more easily fractured) because the other layer(s) may be formed of a material which provide the assembly with the necessary strength, even if the other layer is very thin. In the above example, the steel layers may be very thin yet still able to absorb the load, e.g., the tensile forces that arise during movement of the hollow body or adjacent tissue. The particular overall dimensions of the securing component, as well as the dimensions of individual layer (or layers if a multilayer construction is used) will of course depend on the application. (As examples, for the securing component 22 shown in FIG. 3, the thickness in inches is preferably less than 0.040, and more preferably less than 0.020, e.g., approximately 0.015 or even less, e.g., 0.008.)

The ability to form a very thin securing component allows formation of an anastomosis between relatively small hollow bodies, e.g., coronary blood vessels. Further, the anastomosis can be formed between blood-carrying hollow bodies with one or more of the securing components located in the blood flow path while minimizing the foreign material exposed to blood.

Figure 10B:
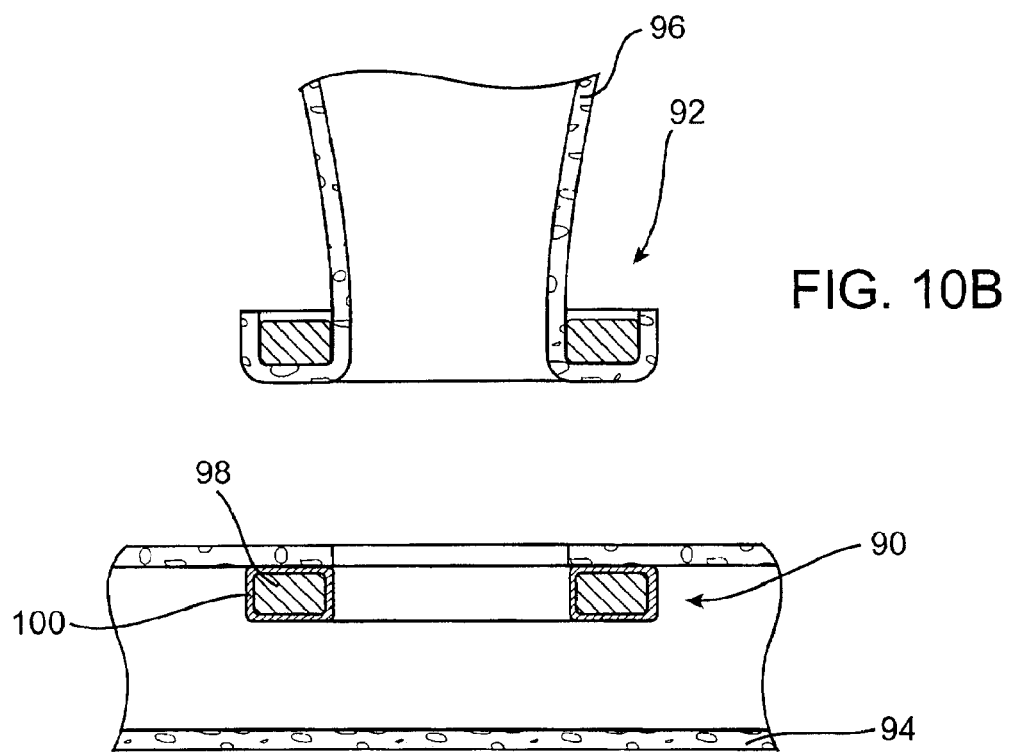
FIG. 10B is a section view similar to FIG. 10A including other alternative anastomotic securing components for joining the two hollow bodies.

FIG. 10B shows first and second securing components 90, 92 coupled to first and second hollow bodies 94, 96. The first securing component 90 comprises a single member 98 positioned within the lumen of the first hollow body 94 against the interior surface of the wall of the body adjacent an opening therein. The member 98 has a coating 100 substantially, and preferably completely, surrounding its exterior surface. It may be desirable in some applications to apply a suitable coating, or alternatively, a suitable surface treatment, to all or part of the anastomotic securing component. For example, if the first hollow body 94 represents a blood vessel such as a coronary or peripheral artery, the securing component 90 will be exposed to the blood flow path. As such, depending on the material used to the form the member 98, it may be desirable or necessary to coat or otherwise treat its surface to promote better thrombogenicity and/or improve flow past the anastomosis site. Some exemplary materials that may be used to coat or otherwise treat an anastomotic securing component constructed according to the invention include Gold, Platinum, Titanium Nitride, Parylene, Silicone, Urethane, Epoxy, Teflon and Polypropylene.

Figure 10C:
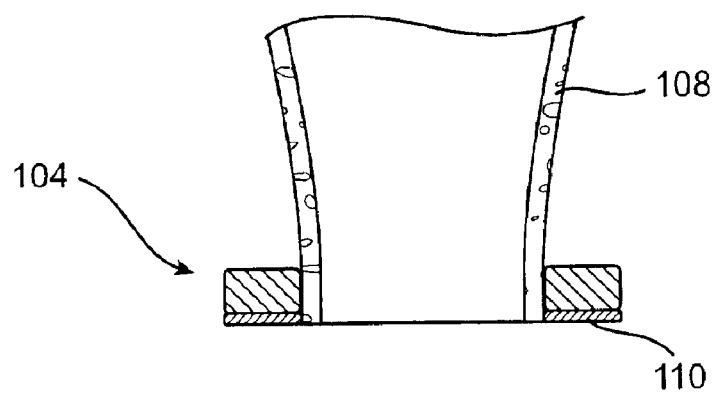
FIG. 10C is a section view similar to FIG. 10A but showing an alternative attachment between a hollow body and an anastomotic securing component.
Figure 10C:
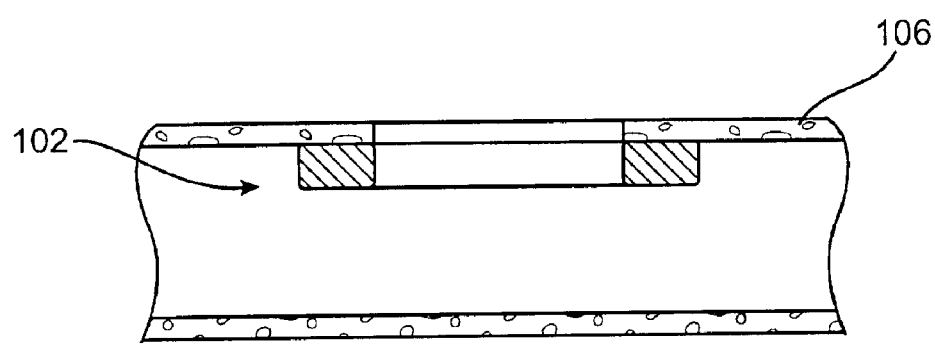

FIG. 10C shows an embodiment wherein first and second securing components 102, 104 are coupled to first and second hollow bodies 106, 108. Each component 102, 104 comprises a single member formed, as explained above, of a magnetic, ferromagnetic, or electromagnetic material. This embodiment, instead of everting an end of one of the hollow bodies 106, 108, provides the first securing component 102 with a portion 110 configured to attach the end of the first hollow body 106. The portion 110 may take various forms, for example, a DACRON® suture ring or bioadhesive. It will be recognized that the portion for attaching the hollow body may be located at different areas of the second securing component 104 than shown in FIG. 10C.

Figure 10D:
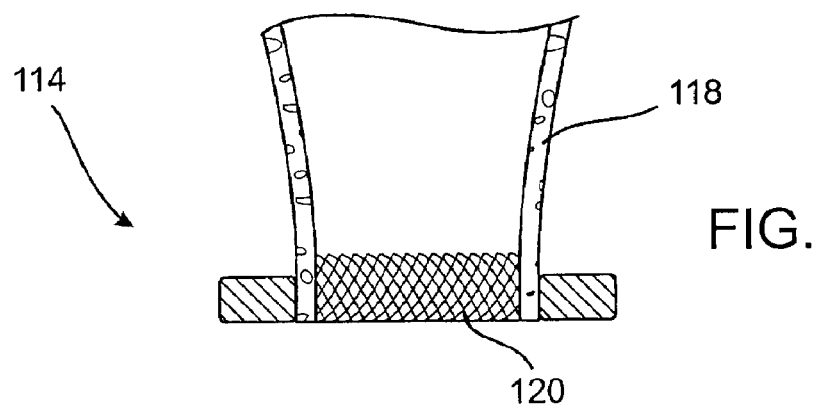
FIG. 10D is a section view similar to FIG. 10C showing another alternative attachment between the hollow body and a securing component.
Figure 10D:
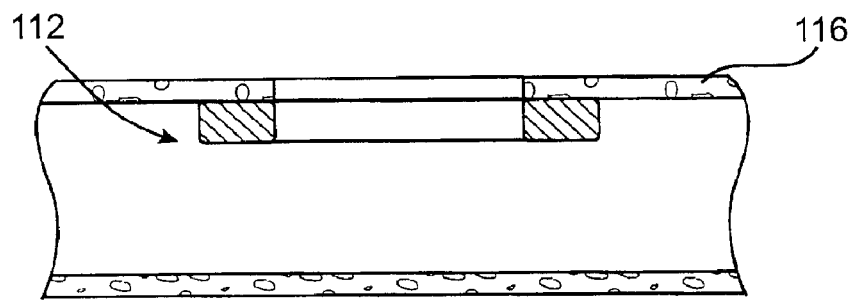

FIG. 10D shows an embodiment of the invention similar to that of FIG. 10C with first and second securing components 112, 114 coupled to first and second hollow bodies 116, 118. The means for attaching the first securing component 112 to the first hollow body 116 in this embodiment comprises an expandable member 120, such as a stent, disposed within the lumen of the first hollow body. The member 120 forces the end of the first hollow body 116 against the first securing component 112 to attach the elements in a fluid-tight fashion. It will be appreciated that the embodiments of FIGS. 10C and 10D are only two of the various ways in which a securing component may be coupled to a hollow body without everting tissue of the hollow body.

Figure 11A:
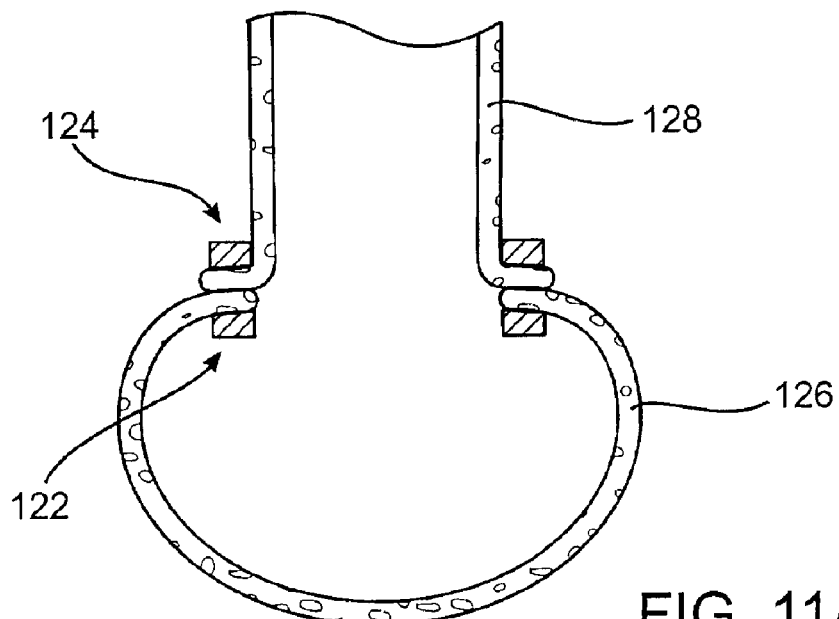
FIG. 11A is a transverse sectional view taken through an end-to-side anastomosis formed according to one embodiment of the invention.
Figure 11B:
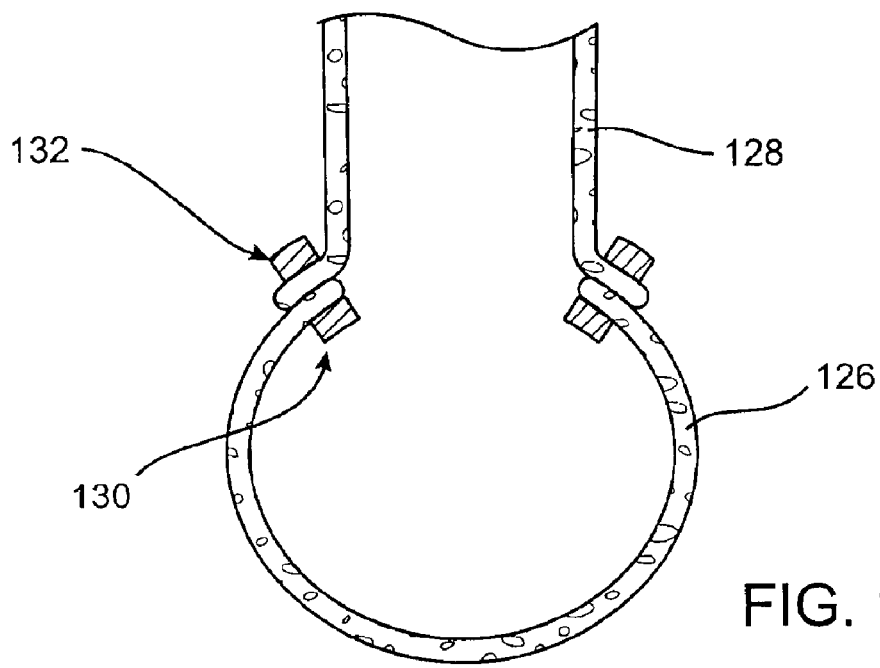
FIG. 11B is a transverse sectional view taken through an end-to-side anastomosis formed according to another embodiment of the invention.

FIG. 11A is a transverse sectional view taken through an end-to-side anastomosis created by first and second securing components 122, 124 which are positioned adjacent openings of first and second hollow bodies 126, 128. The securing components 122, 124 are plate-shaped (as described above) and generally flat. FIG. 11B shows first and second securing components 130, 132 constructed according to an alternative embodiment of the invention positioned adjacent the openings of first and second hollow bodies 126, 128. The securing components 130, 132 are also plate-shaped but, rather than being generally flat, are arcuate or curved. As can be seen, the curvature of the securing components 130, 132 maintains the first hollow body 126 in a substantially round configuration as compared to the more flattened-out shape it assumes when used with the flat securing components 122, 124.

The arcuate securing components 130, 132 preferably have complementarily or substantially complementarily radii of curvature to provide an even distribution of force and good sealing. The securing components of the invention could, however, have different degrees of curvature, the curvature of each being either constant or changing over the body of the component. Also, while the illustrated securing components 130, 132 extend over approximately 120°, other configurations that extend between 0° and 360° could be used if desired, for example, 180°. Finally, while FIGS. 11A and 11B show, respectively, a pair of flat components and a pair of arcuate components, the securing components of each pair used to create the anastomosis may have dissimilar configurations to varying degrees.

Figure 12:
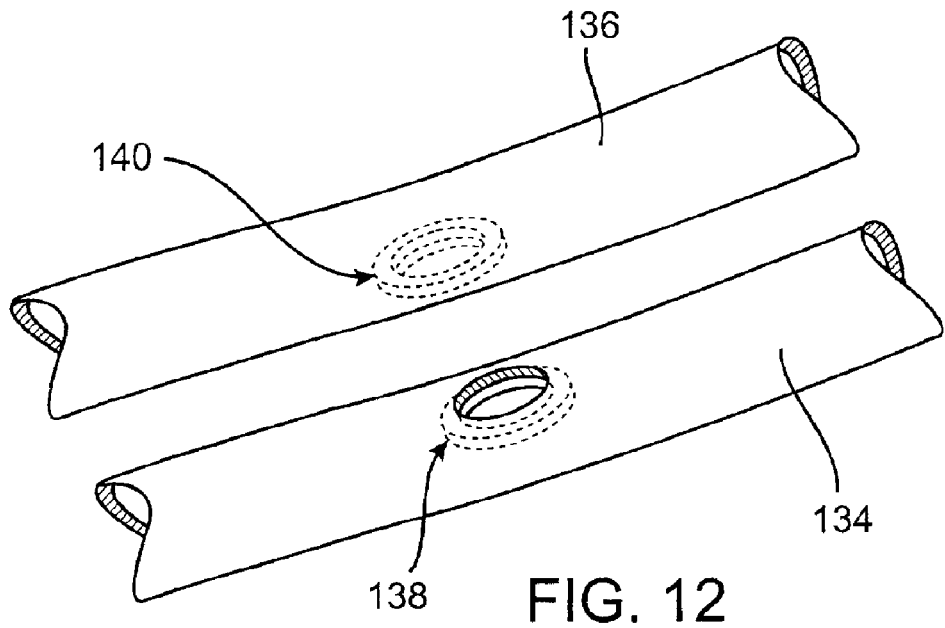
FIG. 12 is a perspective view showing two hollow bodies provided with anastomotic securing components constructed according to one embodiment of the invention, the two bodies adapted to be joined via a side-to-side anastomosis.
Figure 14A:
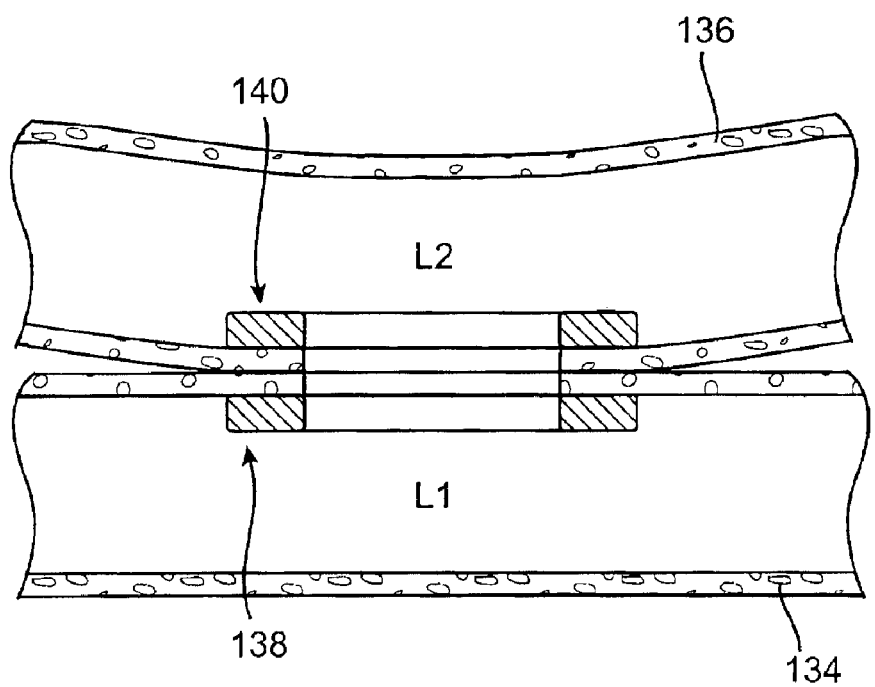
FIG. 14A is a longitudinal sectional view taken through the side-to-side anastomosis formed according to the embodiment shown in FIG. 12.
Figure 14B:
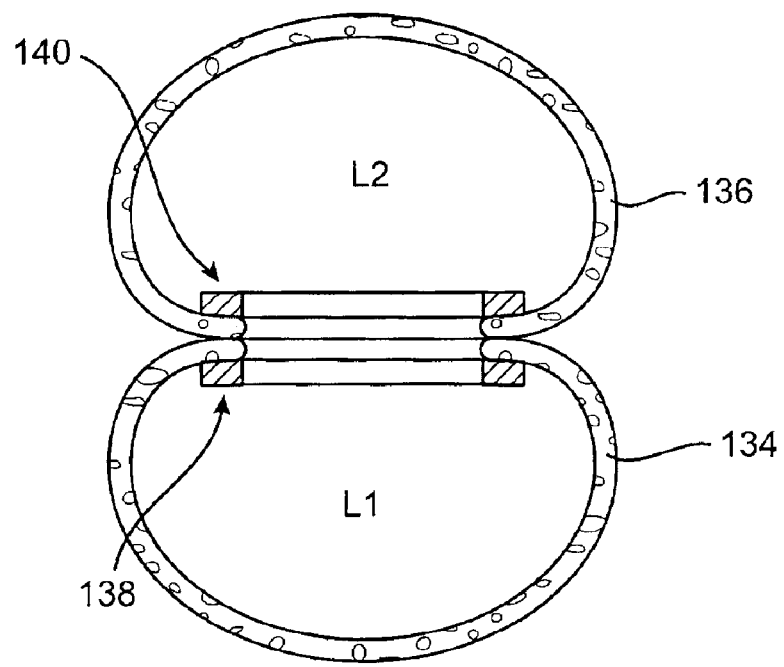
FIG. 14B is a transverse sectional view taken through the side-to-side anastomosis formed according to the embodiment shown in FIG. 12.

FIGS. 12 and 14A–14B show other embodiments of the invention wherein first and second hollow bodies 134, 136 are respectively provided with securing components in order to create a side-to-side anastomosis. The embodiment of FIG. 12 utilizes first and second securing components 138, 140 respectively positioned adjacent openings in the hollow bodies 134, 136. Each securing component 134, 136 includes a single member that may comprise one or more materials and one or more layers, as described above. The components may be fixed by adhesive or other means or remain in position via magnetic force, as explained above. The securing components 138, 140 are positioned through openings formed in the wall of the hollow bodies 134, 136 and are located within the respective lumens L1, L2 thereof, as shown in FIGS. 14A and 14B. Once joined, the components 138, 140 form a fluid-tight anastomosis that places the first and second hollow bodies 134, 136 in communication. If the hollow bodies 134, 136 are blood (or other fluid) carrying structures, the anastomosis places them in fluid communication and provides a fluid-tight seal.

Figure 13:
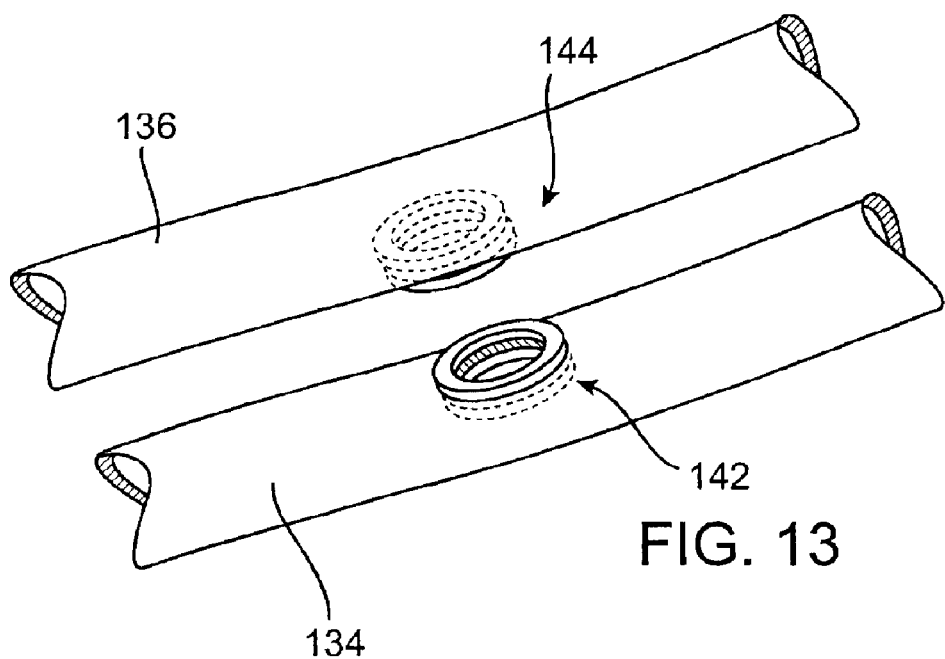
FIG. 13 is a perspective view showing the two hollow bodies of FIG. 12 provided with anastomotic securing components constructed according to another embodiment of the invention.

The embodiment of FIG. 13 uses first and second securing components 142, 144 which are respectively positioned adjacent openings in the hollow bodies 134, 136 so as to be partially disposed within the lumens thereof. The opening in each hollow body may be formed by making a surgical incision, removing tissue with a punch, etc. Each securing component 142, 144 includes a pair of members, and each member may comprise one or more materials and one or more layers. One member of each securing component 142, 144 is positioned within the lumen of its hollow body while the other member of the securing component is positioned on the exterior of the hollow body with tissue captured between the members of each component.

Figure 15:
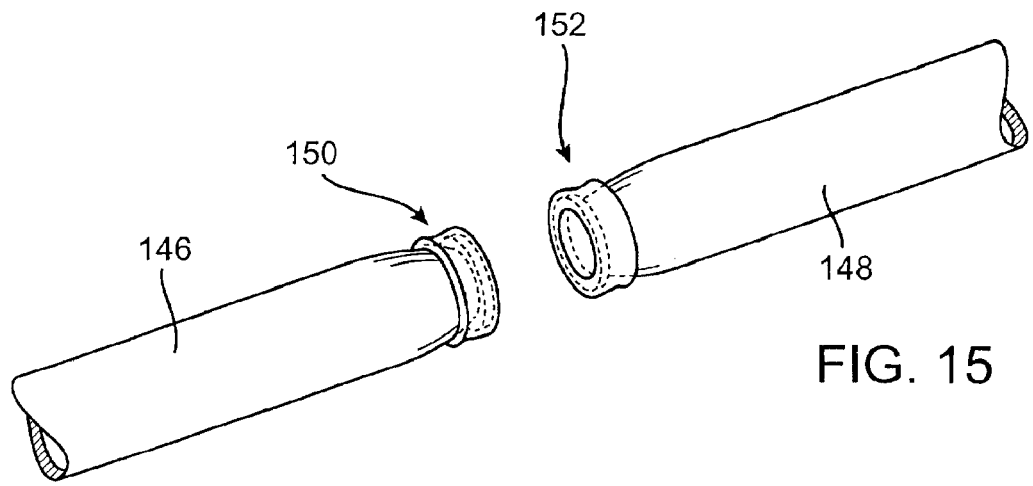
FIG. 15 is a perspective view showing two hollow bodies provided with anastomotic securing components constructed according to one embodiment of the invention, the two bodies adapted to be joined via an end-to-end anastomosis.
Figure 16:
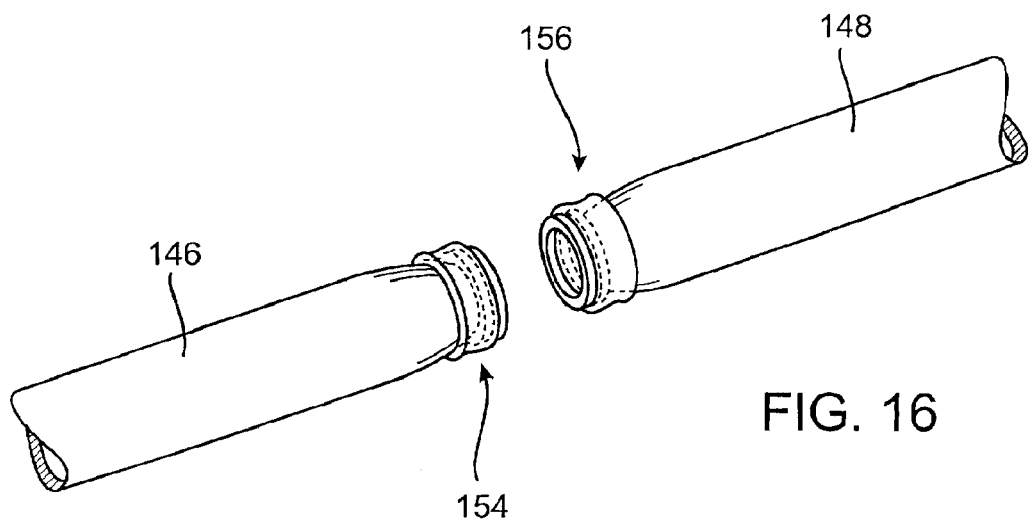
FIG. 16 is a perspective view showing the two hollow bodies of FIG. 15 provided with anastomotic securing components constructed according to another embodiment of the invention.

FIGS. 15 and 16 show further embodiments of the invention wherein first and second hollow bodies 146, 148 are respectively provided with first and second anastomotic securing components in order to create an end-to-end anastomosis. FIG. 15 shows first and second securing components 150, 152 positioned adjacent respective openings of the hollow bodies 146, 148, each opening being defined by an end of a hollow body and extending into the lumen thereof.

Each securing component 150, 152 includes a single member that may be constructed as described above. An end of each hollow body 146, 148 is passed through the opening defined by a respective securing component and is then everted over the exterior of the component. As a result, joining the first and second securing components 150, 152 in end-to-end fashion places the everted ends of the hollow bodies 146, 148 in sealed contact. In a case where the hollow bodies are natural blood vessels, such an anastomosis places the intimal surfaces of the vessels in contact.

The embodiment of FIG. 16 includes first and second securing components 154, 156 positioned adjacent the openings of hollow bodies 146, 148, respectively. The securing components 154, 156 each comprise a pair of members constructed as described above. The first securing component 154 includes one member 154A positioned around the exterior of the first hollow body 146 (with the end thereof everted), and another member 154B positioned around the opening defined by the end of the hollow body 146, the members 154A, 154B being held in place by magnetic force. The second securing component 156 has the same or a similar construction and includes members 156A, 156B which are positioned adjacent the end of the second hollow body 148. In the embodiments of FIGS. 15–16 the securing components are not located within the lumen of either hollow body and thus are not exposed to fluid or other substances contained therein or moving therethrough.

Another embodiment of the invention will be described with reference to FIGS. 17A–17B. FIG. 17A shows a hollow body 160 with an opening 162 and an anastomotic securing component 164 positioned adjacent the opening. The securing component 164 is positioned within the lumen L of the hollow body 160 and has an opening 166. The opening 166 is aligned with the opening 162 in the wall of the body 160 as shown. In some instances, for example, when the securing component is forced through an incision in the wall, the tissue defining the opening 162 may move over the opening 166 of the securing component 164, as shown in FIG. 17B. As indicated by reference numeral 168 in FIG. 17B, this reduces the effective area of the securing component 164 that is available to communicate with a second hollow body to which the hollow body 160 is anastomosed (not shown).

FIG. 18A–18B show the hollow body 160 with the opening 162 of FIGS. 17A–17B, however, a securing component 170 constructed according to another embodiment of the invention is positioned adjacent the opening 162. The securing component 170 has an opening 172 and has a feature for maintaining the opening 162 open to flow. The securing component 170 comprises a flange 174 and an extension 176 coupled thereto (or formed integrally therewith). As can be seen, the extension 174 prevents tissue defining or adjacent the opening 162 of hollow body 160 from migrating or springing back after delivery to reduce the cross-sectional flow area of the securing component 170.

Figure 19A:
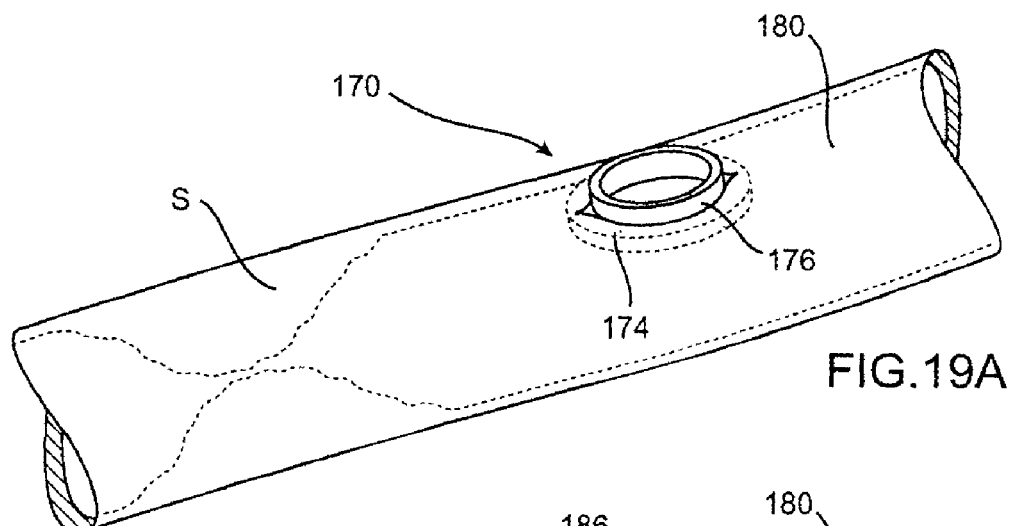
FIG. 19A is a perspective view of the anastomotic securing component shown in FIGS. 18A–18B, the component positioned in an opening in a hollow body with a lumen having a stenosis disposed proximal to the opening.
Figure 19B:
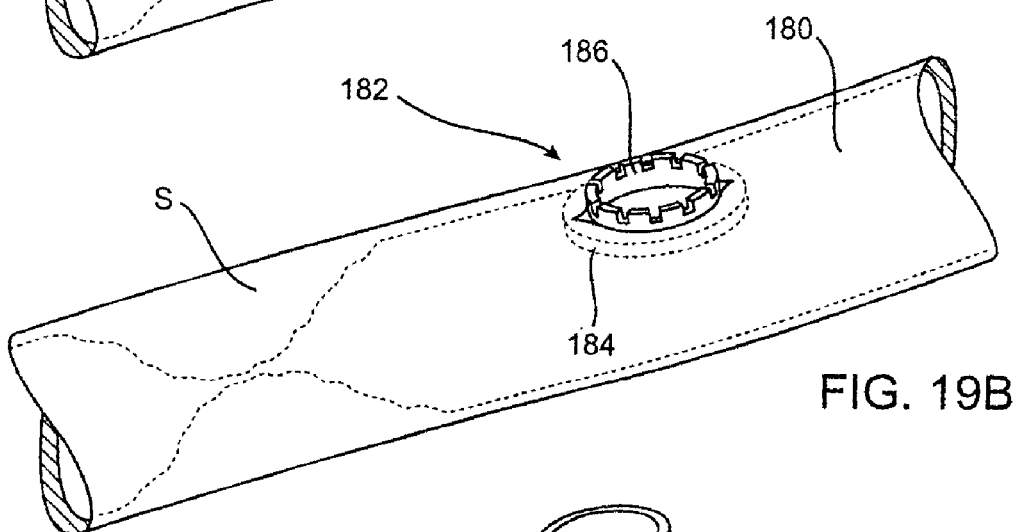
FIGS. 19B–19C show anastomotic securing components constructed according to further alternative embodiments of the invention, the components being shown positioned in the hollow body of FIG. 19A.
Figure 19C:
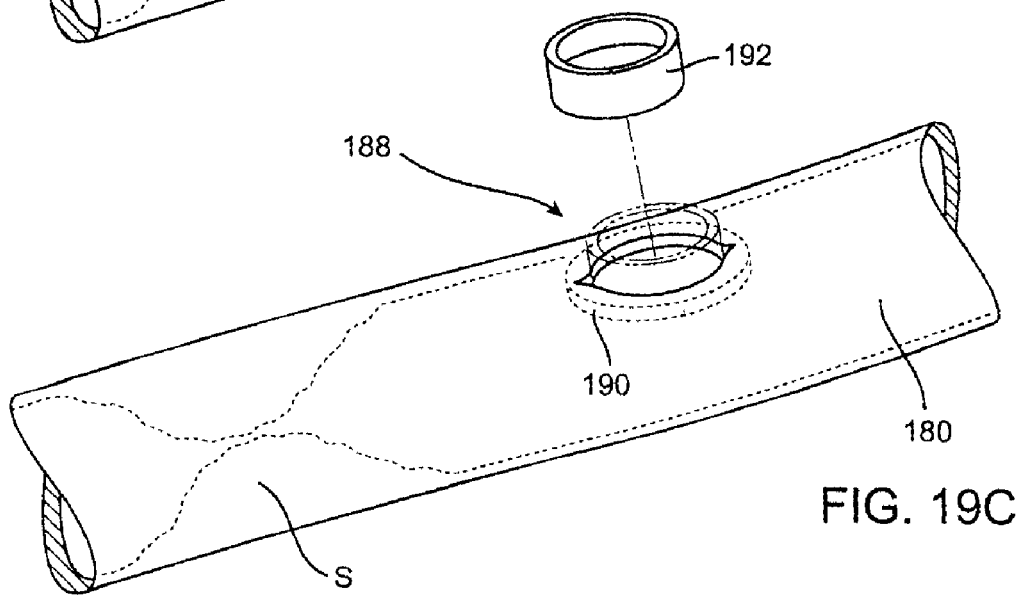

FIGS. 19A–19C show a hollow body 180 which may, for example, represent a patient's coronary or peripheral artery, the lumen of which is stenosed at S. In FIG. 19A, the hollow body 180 is provided with the anastomotic securing component 170 of FIGS. 18A–18B by coupling the securing component to an opening in the wall of the artery, thereby forming a site for creating an end-to-side or side-to-side anastomosis. In FIG. 19B, the hollow body 180 is provided with an alternatively configured anastomotic securing component 182 which includes a flange 184 and a discontinuous or segmented extension 186 passing all or partly through the opening in the wall of the hollow body. FIG. 19C shows a securing component 188 with a multi-part construction including a flange 190 and a separate extension 192 which is received in the opening of the hollow body 180. It should be understood that these are only a few of the various constructions that may be employed in practicing this aspect of the invention.

Figure 20A:
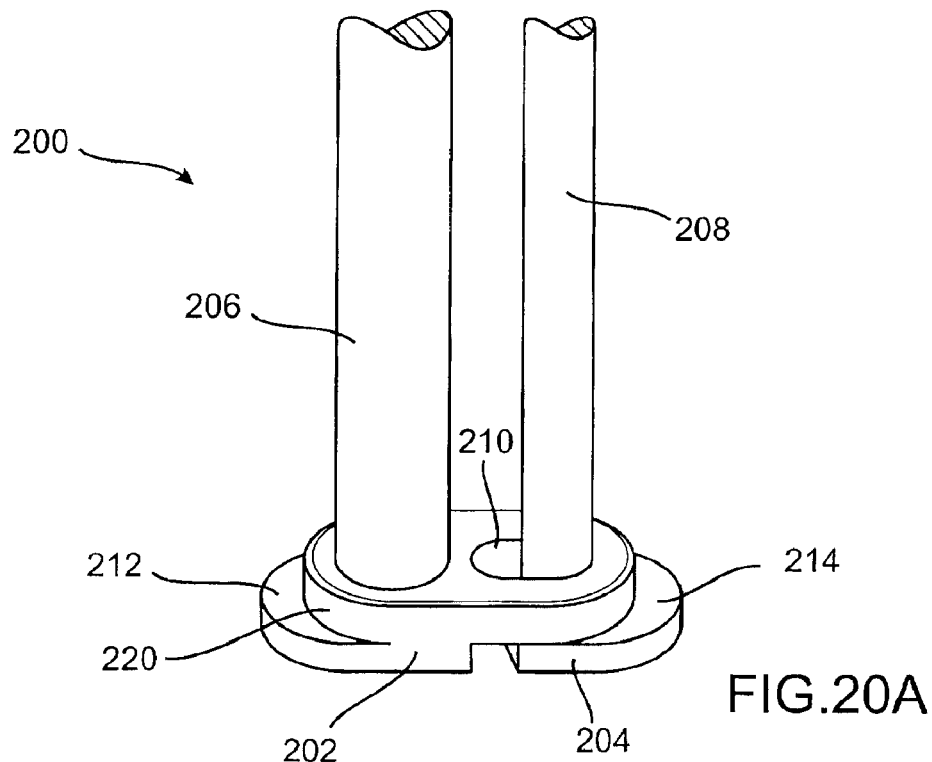
FIG. 20A is a perspective view of a delivery device constructed to one embodiment of the invention, the device being shown in a first position.

The anastomotic securing components of the invention may be delivered and deployed in various ways. FIGS. 20A–20B and 21A–21B depict somewhat schematically an exemplary delivery device 200 including a first portion 202 operatively coupled to a second portion 204. The first portion 202 is fixed to a shaft 206 while the second portion 204 is fixed to shaft 208 passing through a slot 210 in the portion 202. The first portion 202 defines a support ledge 212 and the second portion 202 similarly defines a support ledge 214. FIG. 20A shows the device 200 in a first position for retaining an anastomotic securing component of the invention. This position is shown in FIG. 21A wherein the ledges 212, 214 support a securing component 216 with the opening 218 of the component surrounding a boss 220 that extends-upwardly from the ledges. The boss 220 is preferably used to help align the securing component on the support ledges 212, 214 and, if used in an application with an opening formed in a side wall of a hollow body, to restrain the surrounding tissue during placement.

Figure 20B:
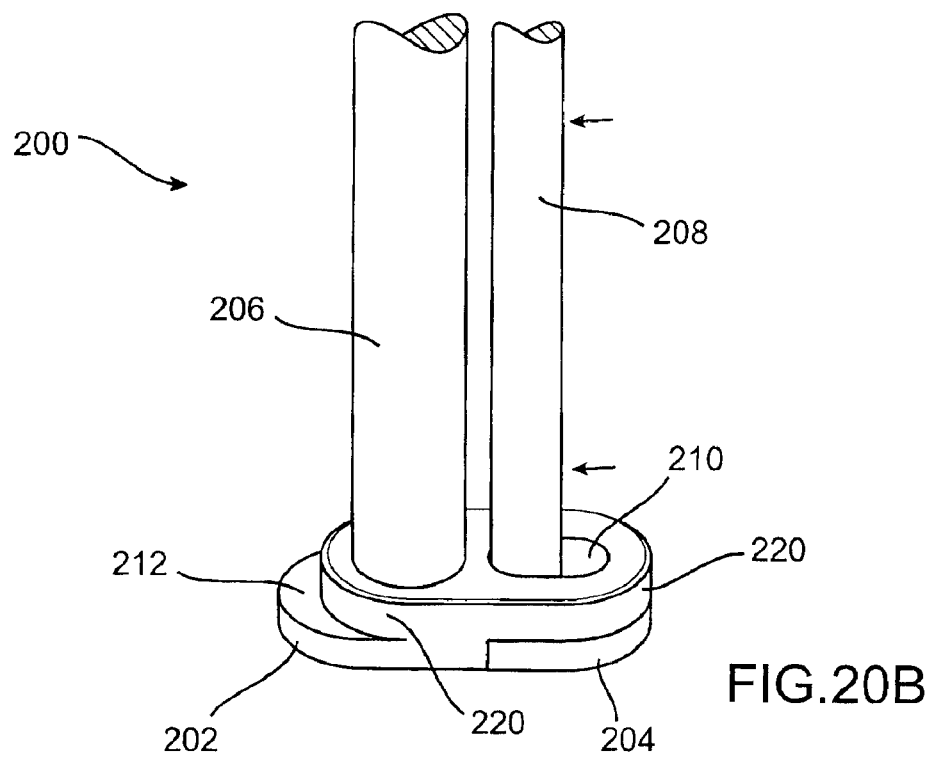
FIG. 20B is a perspective view of the delivery device shown in FIG. 20A, the device being shown in a second position.
Figure 21A:
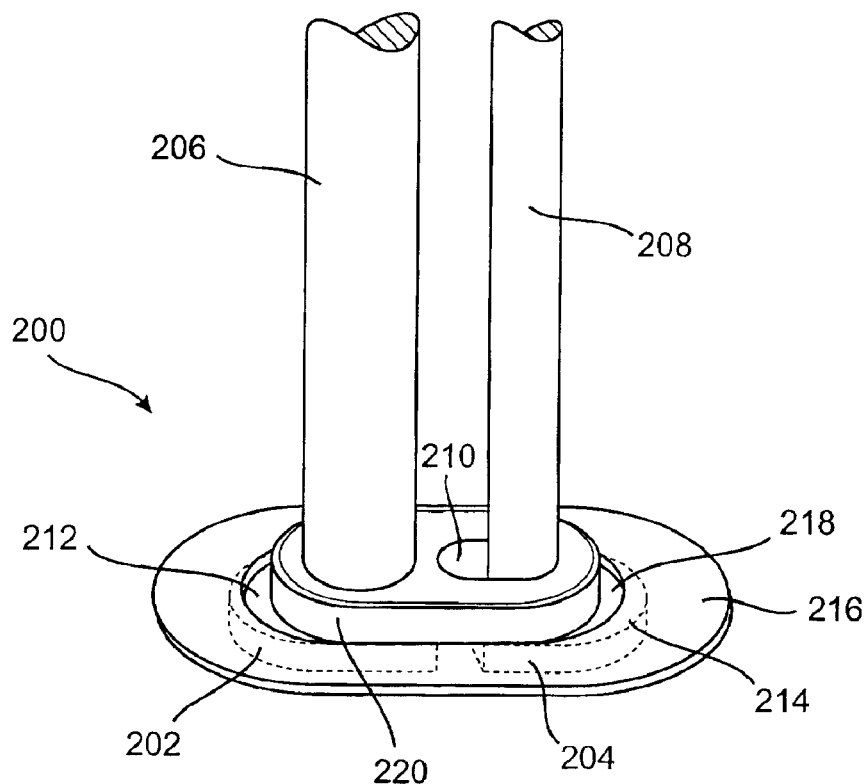
FIG. 21A is a perspective view of the delivery device shown in FIG. 20A with a securing component constructed to one embodiment of the invention mounted thereon, the delivery device being shown in the first position.
Figure 21B:
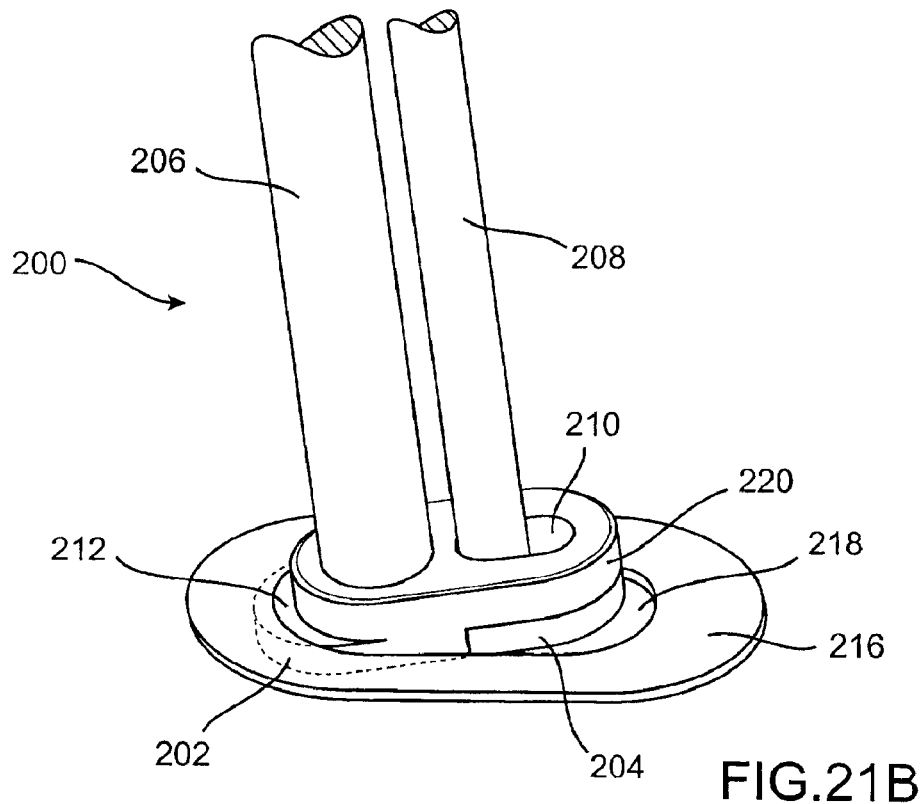
FIG. 21B is a perspective view of the delivery device shown in FIG. 21A, wherein the device is shown in the second position as it is being manipulated to release the securing component.

FIGS. 20B and 21B show the device 200 after it has been moved to a second position from the position of FIGS. 20A and 21A. This is achieved by moving the shaft 208 in the direction of the arrows to slide the second portion 204 with respect to the first portion 202, which moves the support ledge 214 within the opening 218 of the anastomotic securing component 216 (FIG. 21B). This allows the user to separate the device 200 from the securing component 216 once the latter has been positioned at the desired location. As shown, depending on the relative dimensions and shapes of the respective components it may be necessary to rock or otherwise manipulate the device 200 relative to the securing component 216 in order to separate them.

It will be understood that the illustrated delivery device 200 is only one possible device suitable for use in placing the anastomotic securing components of the invention, and that it may be modified or replaced with a different delivery device or system. For example, the delivery device 200 could be altered so that both support ledges 212, 214 are moved with respect to the boss 220 (if used) in order to move fully out of contact with and release the securing component. Any suitable material(s) may be used to construct the delivery device 200, it being appreciated using magnetic or ferromagnetic materials may result in magnetic interaction with the securing components, which may be desired to facilitate delivery of the components. The delivery device could also be constructed of nonmagnetic or ferromagnetic materials such as titanium, polymers, etc.

Figure 22A:
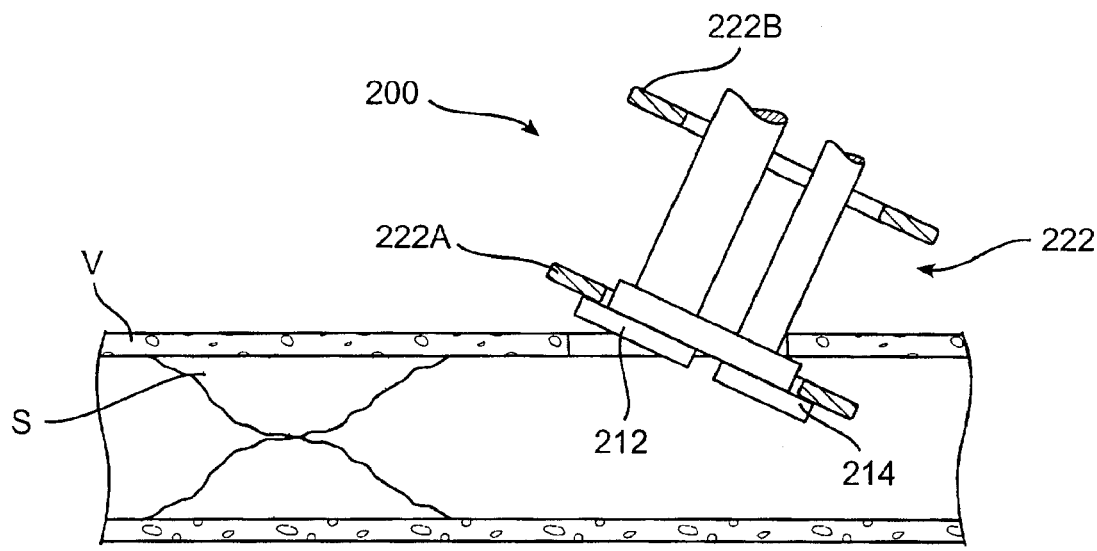
FIGS. 22A–22F are sectional views schematically illustrating the delivery device shown in FIGS. 20A–20B being used to deploy anastomotic securing components to form an end-to-side anastomosis according to one embodiment of the invention.

For sake of example, the creation of an anastomosis using the delivery device 200 and first and second securing components of the invention will be described with respect to FIGS. 22A–22F. FIG. 22A shows the delivery device 200 with a first securing component 222 comprising two members 222A, 222B, the former member being supported by the ledges 212, 214 of the device 200 while the latter member is held above the ledges (e.g., by magnetic attraction to the device 200). The member 222A is being inserted into an opening in the wall of a blood vessel V with a stenosis S. The member 222A may be shaped or otherwise treated to ease insertion into the vessel lumen; for example, the leading edge of the member 222A may be formed as shown in the embodiment of FIG. 5.

Figure 22B:
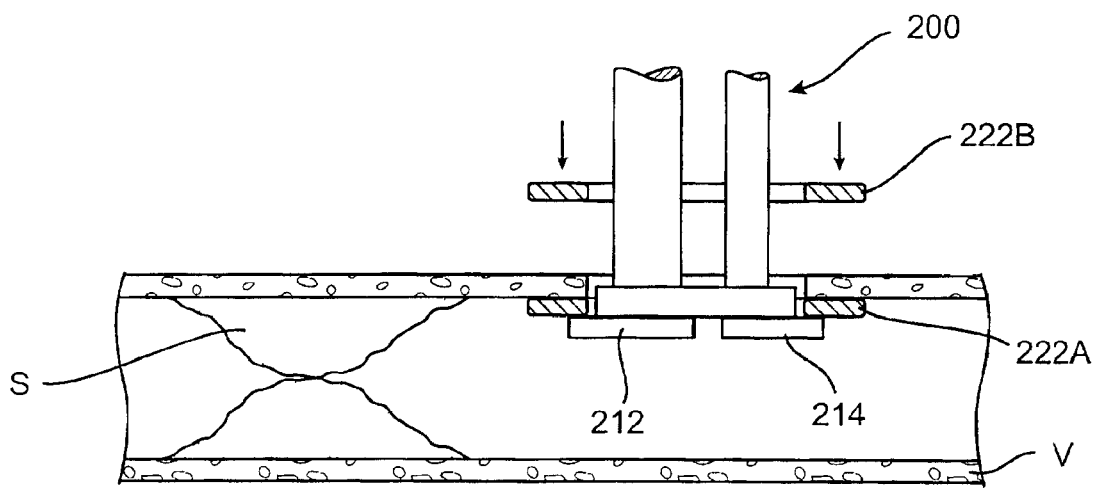
Figure 22C:
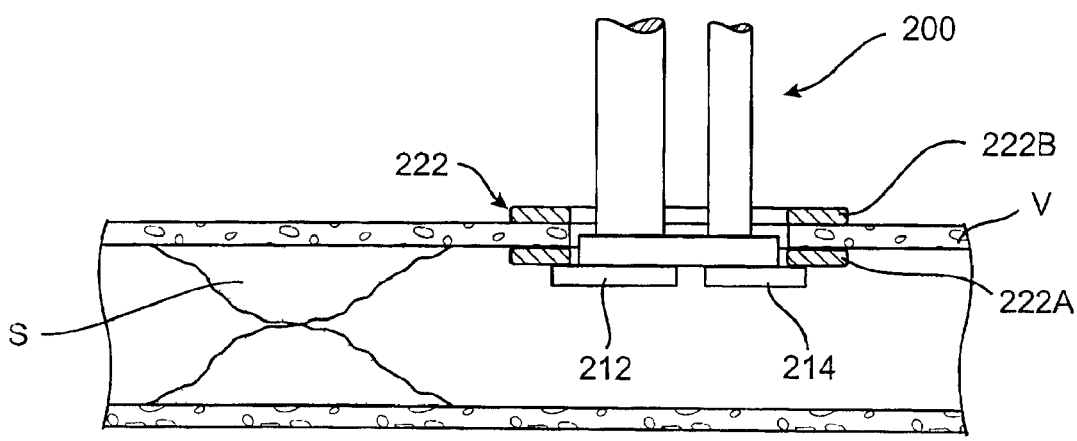
Figure 22D:
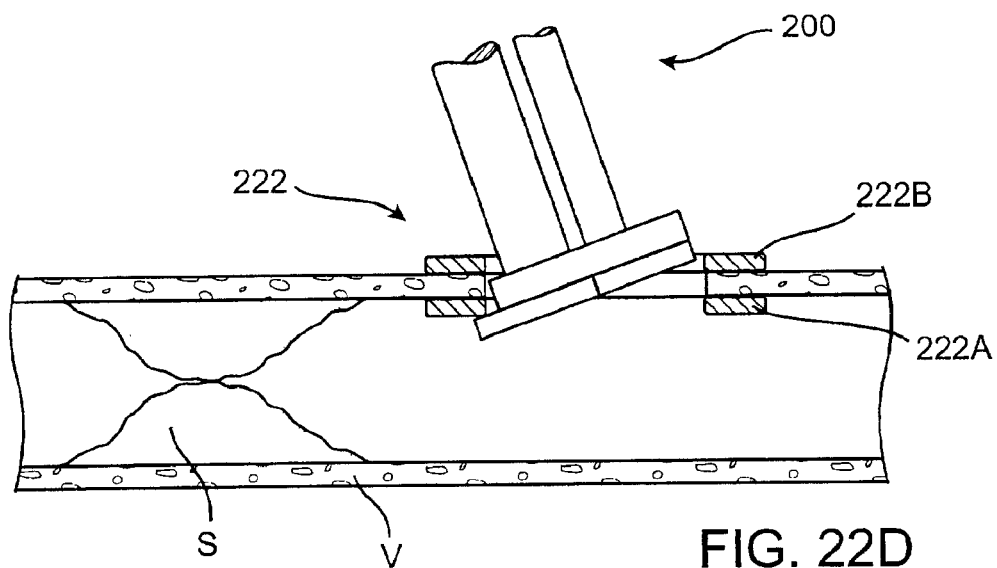
Figure 22E:
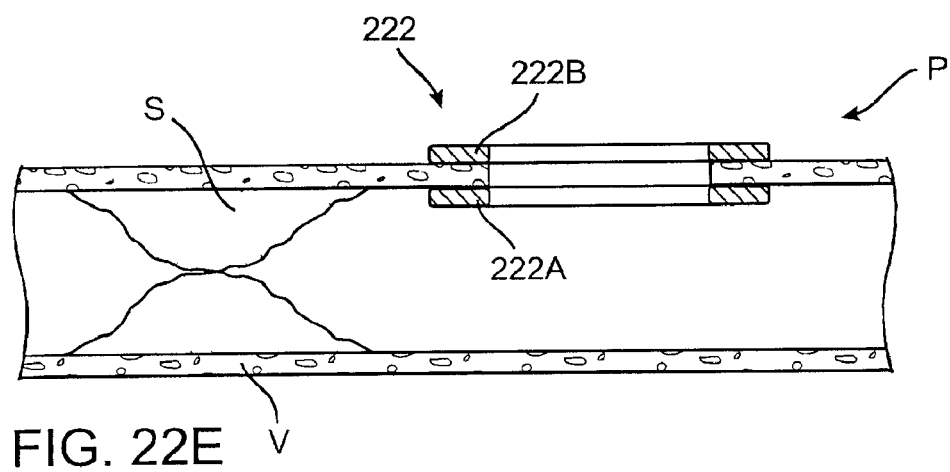

FIG. 22B shows the one member 222A of securing component 222 positioned against the interior surface of the wall of the vessel and the other member 222B being moved toward the vessel wall. FIG. 22C shows the members 222A, 222B in position with the delivery device 200 remaining. FIG. 22D shows the device 200 being removed through first securing component 222, and FIG. 22E shows the securing component 222 remaining in the vessel wall to form what may be characterized as a magnetic port P. The securing component(s) may be provided with a surface treatment, such as coatings, roughened or treated areas, or mechanical projections, to enhance engagement with the wall of the hollow body.

Figure 22F:
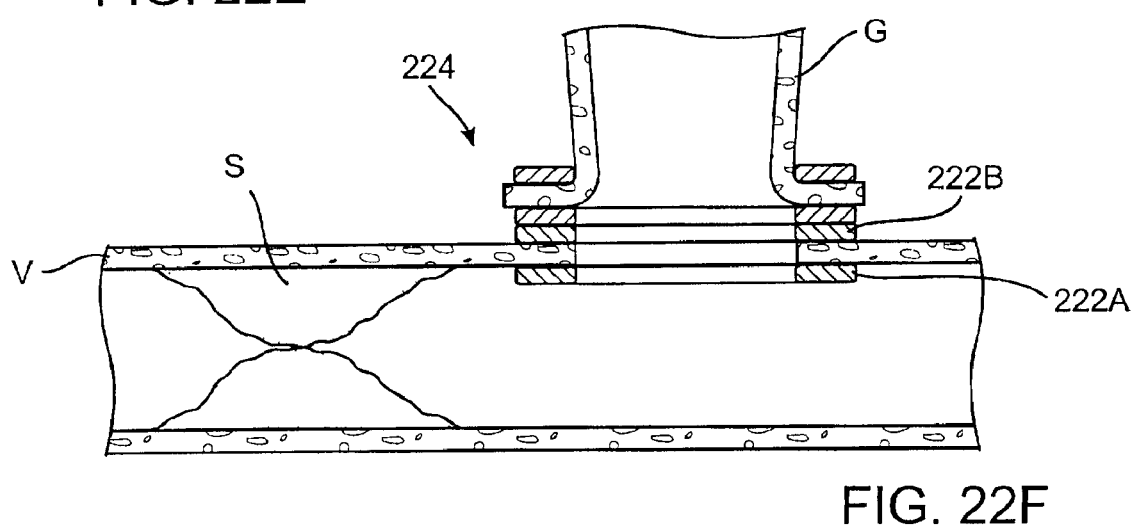

The illustrated securing component 222 defines the magnetic port P and produces a magnetic field that may be used to couple another vessel to the port. In FIG. 22F, a graft vessel G provided with a second securing component 224 (which itself includes two members) is anastomosed to the port P with magnetic force holding the first and second securing components 222, 224 in a desired relative position. The invention may also be practiced using means for fixing the relative distance between the first and second securing components, for example, to prevent tissue being forced or squeezed from the space between the components due to the application of the magnetic force over time. Such means could comprise projections that extend directly between the components and act as a stop, or an intermediate element coupled to the components to restrain them against further movement. It will be recognized that forming a magnetic port according to the invention may also be used in non-vascular applications, as well as applications not requiring an anastomosis to another vessel, for example, to provide an access to an area of a patient's body.

Figure 23:
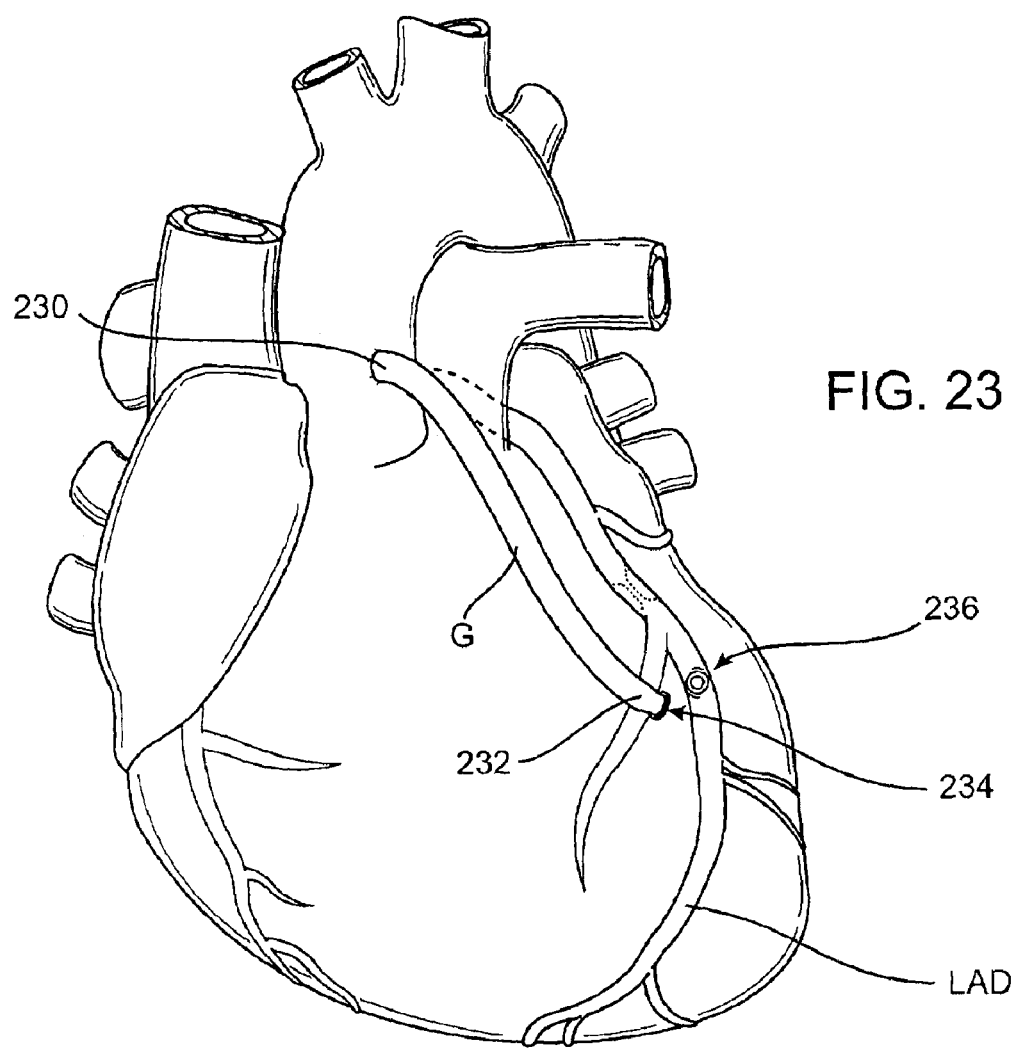
FIG. 23 is a perspective view of an exemplary application according to one embodiment of the invention.
Figure 23A:
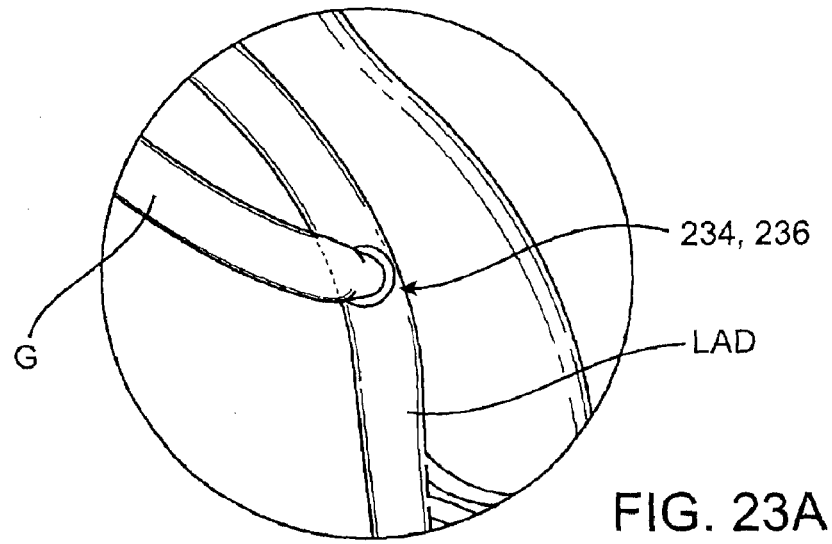
FIG. 23A is an enlarged view of a portion of the embodiment of FIG. 23 but showing a completed anastomosis.

Several exemplary applications of the invention will be described with reference to FIGS. 23–23A, 24–24A and 23–25A. FIG. 23 is an anterior view of a human heart with a graft vessel G having one end 230 attached to the aorta, e.g., by a sutured anastomosis, and another end 232 prepared to be anastomosed to an occluded LAD. One securing component 234 is coupled to the end 232 of the graft G by any of the methods described above, and another securing component 236 is coupled to the LAD adjacent an opening therein. The securing components 234, 236 are formed (at least in part) of materials capable of producing a magnetic field so that they may be attached as shown in FIG. 23A, thereby placing the graft G in fluid communication with the lumen of the LAD. The graft G could alternatively be attached to the aorta by an anastomotic system constructed according to the invention.

Figure 24:
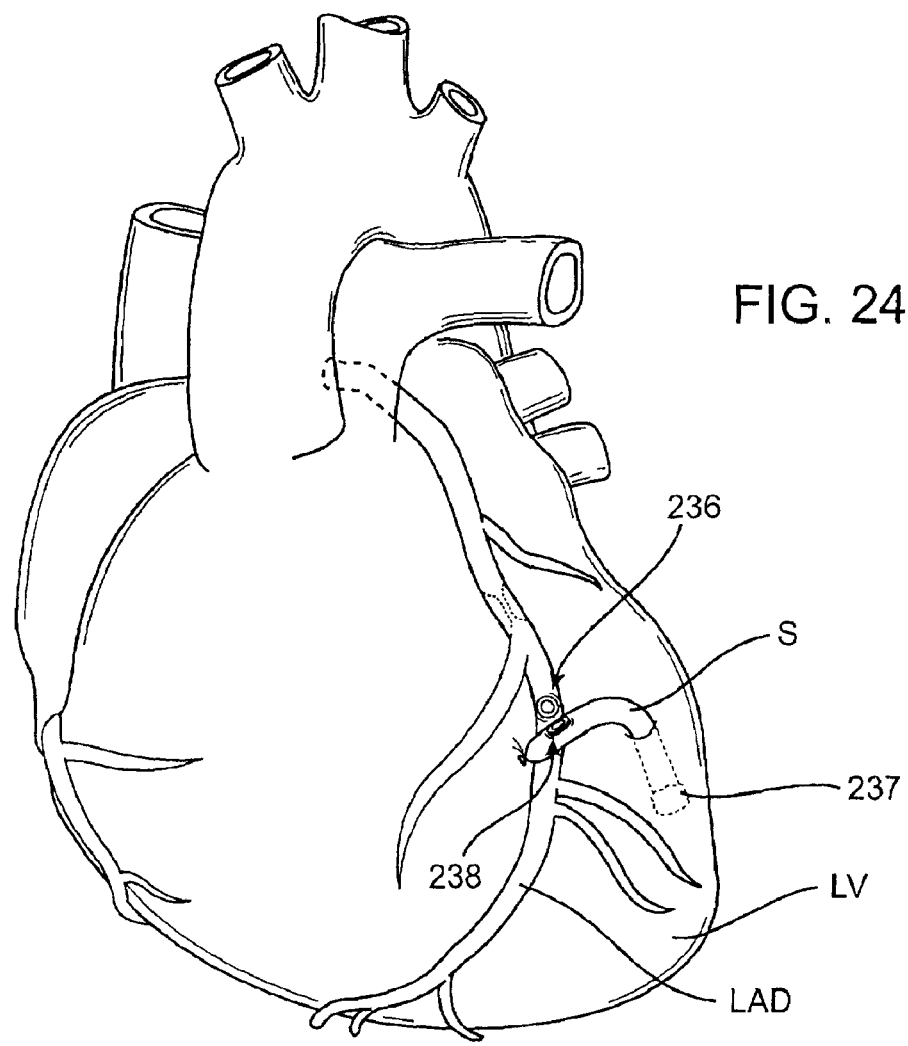
FIG. 24 is a perspective view of another exemplary application according to another embodiment of the invention.
Figure 24A:
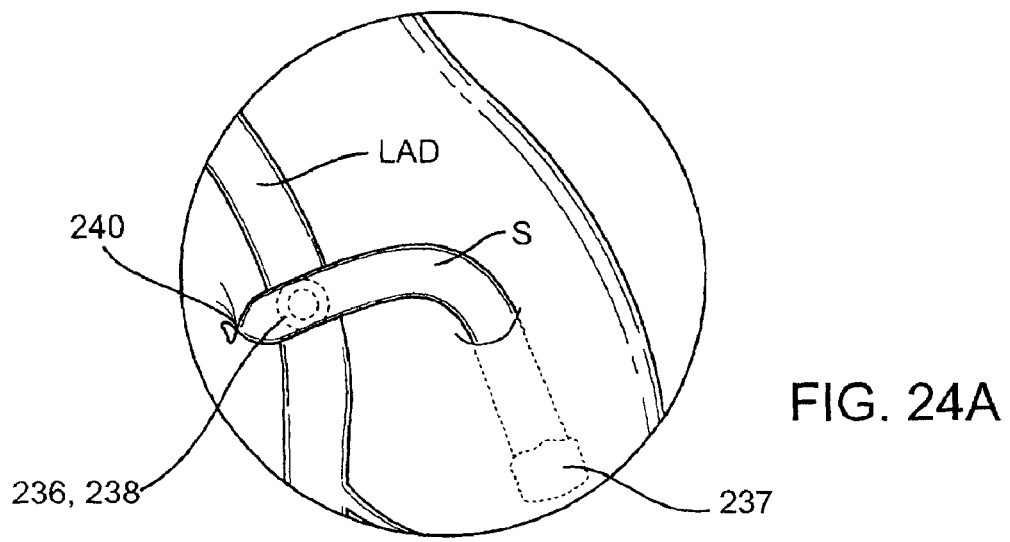
FIG. 24A is an enlarged view of a portion of the embodiment of FIG. 24 but showing a completed anastomosis.

FIG. 24 shows another exemplary application of the invention applied to the heart shown in FIG. 23. A ventriculocoronary shunt S has one end 237 placed in the myocardium in fluid communication with the left ventricle LV. The shunt S is provided with a securing component 238 adjacent its other end while the LAD is provided with the securing component 236 of FIG. 23. The shunt S is adapted to be coupled to the LAD via a side-to-side anastomosis, therefore the securing component 238 is positioned in an opening in the side wall of the shunt (and the free end of the shunt is tied off at 240). FIG. 24A shows the completed anastomosis once the securing components 236, 238 have been coupled and remain in position via the magnetic field produced according to the teachings of the invention.

Figure 25:
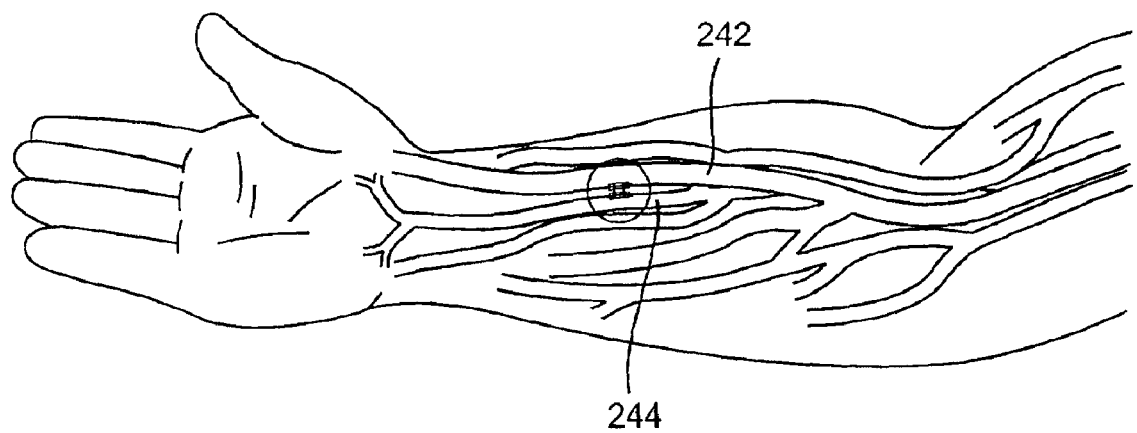
FIG. 25 is a perspective view of an exemplary application according to still another embodiment of the invention.
Figure 25A:
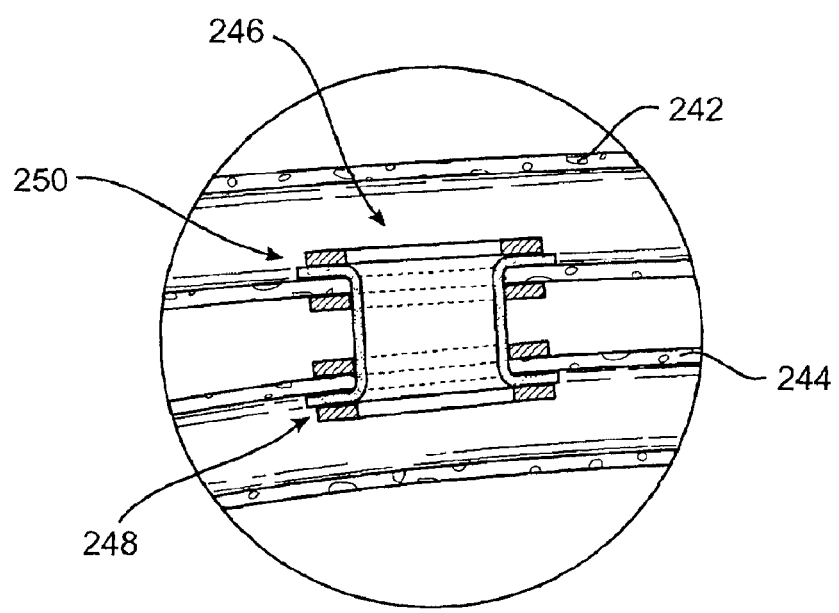
FIG. 25A is an enlarged view of a portion of the embodiment of FIG. 25 but showing a completed AV shunt with two anastomoses.

FIGS. 25–25A illustrate yet another example of the many different applications of the invention, namely, the creation of an AV shunt. FIG. 25 shows a patient's arm including a number of the blood vessels located therein. An artery 242 is shown disposed in relatively close proximity to a vein 244. AV shunts are often created between an artery and vein in order to provide a site for repeatedly accessing a patient's vascular system, for example, to treat dialysis patients. The shunt itself is typically formed of synthetic graft material and can withstand repeated needle sticks much better than a natural vein. An AV shunt 246 is created between the artery 242 and vein 244 by forming a side-to-side anastomosis using first and second securing components 248, 250. The shunt 246 is preferably formed of ePTFE, DACRON® or another suitable synthetic graft material.

It should be appreciated that the applications of FIGS. 23–23A, 24–24A and 23–25A represent several of many different uses for the invention. Other applications for the invention include, for example, neurological, urological and gastrointestinal procedures. As a further example, the invention could be used to form an anastomosis with an existing CABG graft that has partially or completely occluded over time, for instance, by placing the anastomotic securing components in the graft distal to the occlusion. In short, it will be recognized that the invention may be modified in varying degrees from the preferred embodiments illustrated and described specifically herein.

As noted above, it will be recognized that the invention may be used in many different procedures, for example, femoral-femoral, femoral-popliteal, femoral-tibial, tibial, ilio-femoral, axillary-femoral, subclavian-femoral, aortic-bifemoral, aorto-iliac, aorto-profunda femoris and extra-anatomic bypasses. In sum, the invention may be used to create an anastomosis with many different vessels, including, without limitation, the renal arteries, mesenteric vessel, inferior mesenteric artery, eroneal trunk, peroneal and tibial arteries.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A method for forming an anastomosis between first and second vessels using magnetic force, the method comprising steps of:
    selecting a first vessel having a lumen;
    selecting a second vessel having a lumen;
    securing a first anastomotic component to the first vessel;
    securing a second anastomotic component to the second vessel; and
    using magnetic force to create an anastomosis between the first and second vessels with the first anastomotic component contacting the second anastomotic component.

2. The method of claim 1, wherein the first vessel is a coronary artery and the second vessel is a graft selected from the group consisting of natural blood vessels and vessels formed of synthetic material.

3. The method of claim 1, wherein the magnetic force is sufficient to maintain the anastomosis between the first and second vessels.

4. The method of claim 3, wherein only magnetic force is used to form the anastomosis between the first and second vessels.

5. The method of claim 1, further comprising the step of maintaining a full size of an opening in the first vessel.

6. The method of claim 1, wherein each of the first and second anastomotic components includes a material selected from the group consisting of magnetic, electromagnetic and ferromagnetic materials.

7. The method of claim 1, further comprising the step of preventing the first and second anastomotic components from moving toward each other beyond a predetermined distance.

8. The method of claim 1, wherein at least one of the first and second anastomotic components is secured to a respective vessel without penetrating the tissue of the vessel.

9. The method of claim 1, wherein at least one of the first and second anastomotic components is secured to a respective vessel without everting the vessel.

10. The method of claim 9, wherein the first and second anastomotic components are secured to the respective vessels without everting either vessel.

11. The method of claim 1, wherein the securing step is carried out with the first anastomotic component compressing the first vessel.

12. The method of claim 1, further comprising the step of forming a magnetic anastomosis between the second vessel and a third vessel so as to place the third vessel in communication with the first vessel.

13. The method of claim 12, wherein the first and second anastomotic components are separate and physically unconnected.

14. A method for forming an anastomosis between first and second vessels using magnetic force, the method comprising steps of:
    selecting a first vessel having a lumen;
    selecting a second vessel having a lumen;
    securing a first anastomotic component to the first vessel;
    securing a second anastomotic component to the second vessel; and using magnetic force to create an anastomosis between the first and second vessels with the first anastomotic component contacting the second vessel.

15. The method of claim 14, wherein the first vessel is a coronary artery and the second vessel is a graft selected from the group consisting of natural blood vessels and vessels formed of synthetic material.

16. The method of claim 14, wherein the second vessel is a coronary artery and the first vessel is a graft selected from the group consisting of natural blood vessels and vessels formed of synthetic material.

17. The method of claim 14, wherein the magnetic force is sufficient to maintain the anastomosis between the first and second vessels.

18. The method of claim 17, wherein only magnetic force is used to form the anastomosis between the first and second vessels.

19. The method of claim 14, further comprising the step of maintaining a full size of an opening in the first vessel.

20. The method of claim 14, wherein each of the first and second anastomotic components includes a material selected from the group consisting of magnetic, electromagnetic and ferromagnetic materials.

21. The method of claim 14, further comprising the step of preventing the first and second anastomotic components from moving toward each other beyond a predetermined distance.

22. The method of claim 14, wherein at least one of the first and second anastomotic components is secured to a respective vessel without penetrating the tissue of the vessel.

23. The method of claim 14, wherein at least one of the first and second anastomotic components is secured to a respective vessel without everting the vessel.

24. The method of claim 23, wherein the first and second anastomotic components are secured to the respective vessels without everting either vessel.

25. The method of claim 14, further comprising the step of forming a magnetic anastomosis between the second vessel and a third vessel so as to place the third vessel in communication with the first vessel.

26. The method of claim 25, wherein the first and second anastomotic components are separate and physically unconnected.

* * * * *